(12) United States Patent
Karmonik et al.

(10) Patent No.: US 8,170,307 B2
(45) Date of Patent: May 1, 2012

(54) AUTOMATED WALL MOTION QUANTIFICATION IN AORTIC DISSECTIONS

(75) Inventors: Christof Karmonik, Sugar Land, TX (US); Alan B. Lumsden, Hitchock, TX (US)

(73) Assignee: The Methodist Hospital, Houston, TX (US)

( * ) Notice: Subject to any disclaimer, the term of this patent is extended or adjusted under 35 U.S.C. 154(b) by 853 days.

(21) Appl. No.: 12/284,594

(22) Filed: Sep. 23, 2008

(65) Prior Publication Data

US 2010/0074494 A1 Mar. 25, 2010

(51) Int. Cl.
*G06K 9/00* (2006.01)

(52) U.S. Cl. ........ 382/128; 382/130; 382/131; 600/410; 600/420

(58) Field of Classification Search .......................... None
See application file for complete search history.

(56) References Cited

U.S. PATENT DOCUMENTS

| | | | |
|---|---|---|---|
| 4,565,968 A | 1/1986 | Macovski | |
| 4,574,240 A * | 3/1986 | Libove et al. | 324/306 |
| 4,698,592 A | 10/1987 | Feinberg | |
| 4,716,367 A | 12/1987 | Patz | |
| 4,727,882 A | 3/1988 | Schneider et al. | |
| 4,739,766 A | 4/1988 | Riederer | |
| 4,782,834 A | 11/1988 | Maguire et al. | |
| 4,855,910 A | 8/1989 | Bohning | |
| 4,940,055 A | 7/1990 | Brown | |
| 5,016,637 A | 5/1991 | Koizumi et al. | |
| 5,042,485 A | 8/1991 | Sano et al. | |
| 5,107,838 A | 4/1992 | Yamaguchi | |
| 5,195,525 A | 3/1993 | Pelc | |
| 5,320,099 A | 6/1994 | Roberts et al. | |
| 5,329,925 A | 7/1994 | NessAiver | |
| 5,394,872 A | 3/1995 | Takiguchi et al. | |
| 5,417,213 A | 5/1995 | Prince | |
| 5,474,067 A | 12/1995 | Laub | |
| 5,517,120 A | 5/1996 | Misic et al. | |
| 5,545,993 A | 8/1996 | Taguchi et al. | |
| 5,579,767 A | 12/1996 | Prince | |
| 5,590,654 A | 1/1997 | Prince | |
| 5,636,636 A | 6/1997 | Kuhn et al. | |
| 5,680,862 A | 10/1997 | Song et al. | |
| 5,682,883 A | 11/1997 | Fiat | |
| 5,685,300 A | 11/1997 | Kuenstner | |
| 5,792,056 A | 8/1998 | Prince | |
| 5,799,649 A | 9/1998 | Prince | |
| 5,800,354 A | 9/1998 | Hofland et al. | |

(Continued)

FOREIGN PATENT DOCUMENTS

WO  WO 2006079018 A2 *  7/2006

OTHER PUBLICATIONS http://rsb.info.nih.gov/ij/, National Institutes of Health, (2008).

(Continued)

*Primary Examiner* — Minh N Tang

(57) ABSTRACT

A computer implemented method of processing MRI images to determine one or more characteristics of an anatomical feature that includes obtaining one or more first MRI images of the anatomical feature; identifying a boundary of an anatomical feature in the MRI images; and using the identified boundary to mask one or more corresponding second MRI images of the anatomical feature to isolate the anatomical feature within the second MRI images.

56 Claims, 33 Drawing Sheets

U.S. PATENT DOCUMENTS

| | | | |
|---|---|---|---|
| 5,823,960 A | 10/1998 | Young et al. | |
| 5,853,365 A | 12/1998 | Yamagata | |
| 5,924,987 A | 7/1999 | Meaney et al. | |
| 5,969,525 A | 10/1999 | Van Driel et al. | |
| 5,977,769 A | 11/1999 | Bornert et al. | |
| 6,205,871 B1 | 3/2001 | Saloner et al. | |
| 6,237,605 B1 | 5/2001 | Vaska et al. | |
| 6,240,311 B1 | 5/2001 | Prince | |
| 6,408,202 B1 | 6/2002 | Lima et al. | |
| 6,442,415 B1 | 8/2002 | Bis et al. | |
| 6,463,318 B2 | 10/2002 | Prince | |
| 6,511,325 B1 | 1/2003 | Lalka et al. | |
| 6,559,641 B2 | 5/2003 | Thesen | |
| 6,564,085 B2 | 5/2003 | Meaney et al. | |
| 6,662,038 B2 | 12/2003 | Prince | |
| 6,702,847 B2 | 3/2004 | DiCarlo | |
| 6,754,376 B1 | 6/2004 | Turek et al. | |
| 6,798,199 B2 | 9/2004 | Larson et al. | |
| 6,889,072 B2 | 5/2005 | Prince | |
| 7,110,806 B2 | 9/2006 | Prince | |
| 7,319,328 B1 | 1/2008 | Karmonik | |
| 7,344,561 B2 | 3/2008 | DiCarlo | |
| 7,389,776 B2 | 6/2008 | Maksimovich | |
| 2003/0163036 A1* | 8/2003 | Prince | 600/420 |
| 2005/0156593 A1* | 7/2005 | Assmann et al. | 324/306 |
| 2005/0165294 A1* | 7/2005 | Weiss | 600/410 |

OTHER PUBLICATIONS

International Search Report (PCT/US2009/057843), dated Nov. 17, 2009.

* cited by examiner

102a

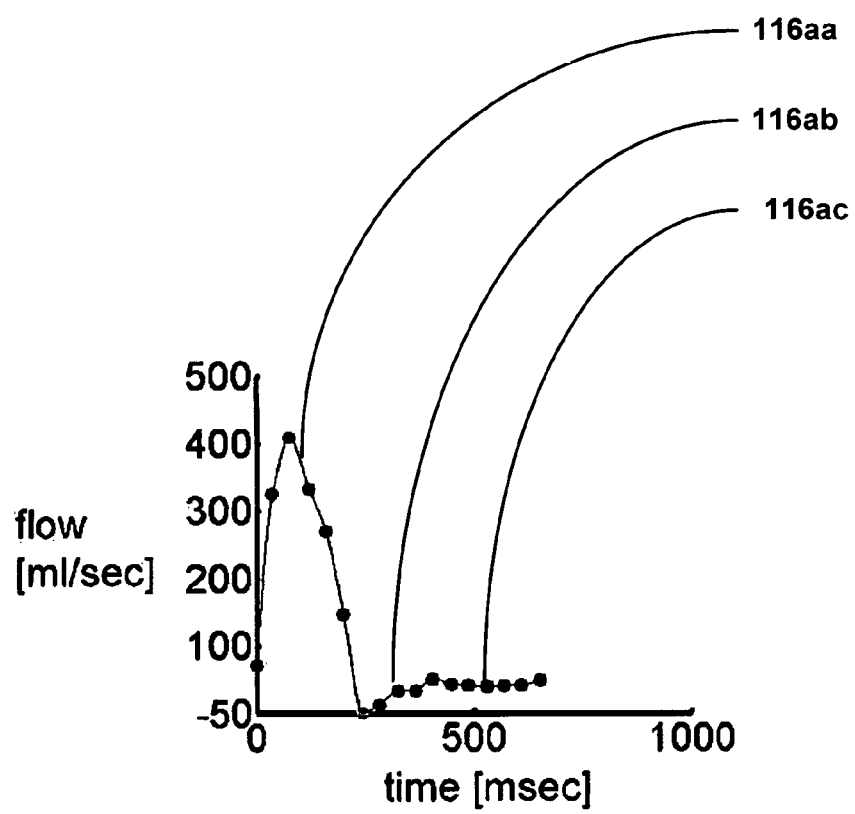
Fig. 8

120a

1504a

1506a

1508a

1516a

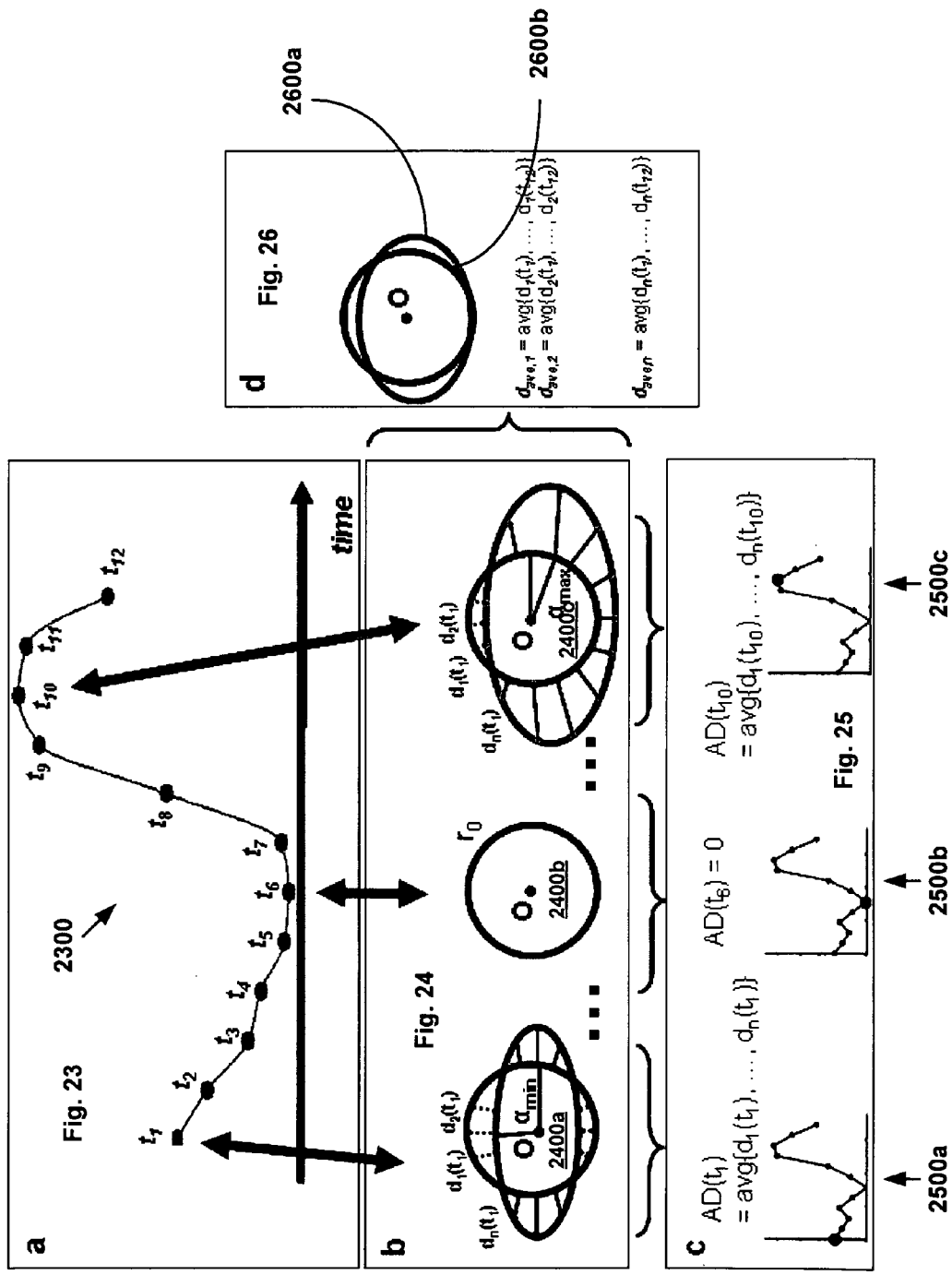

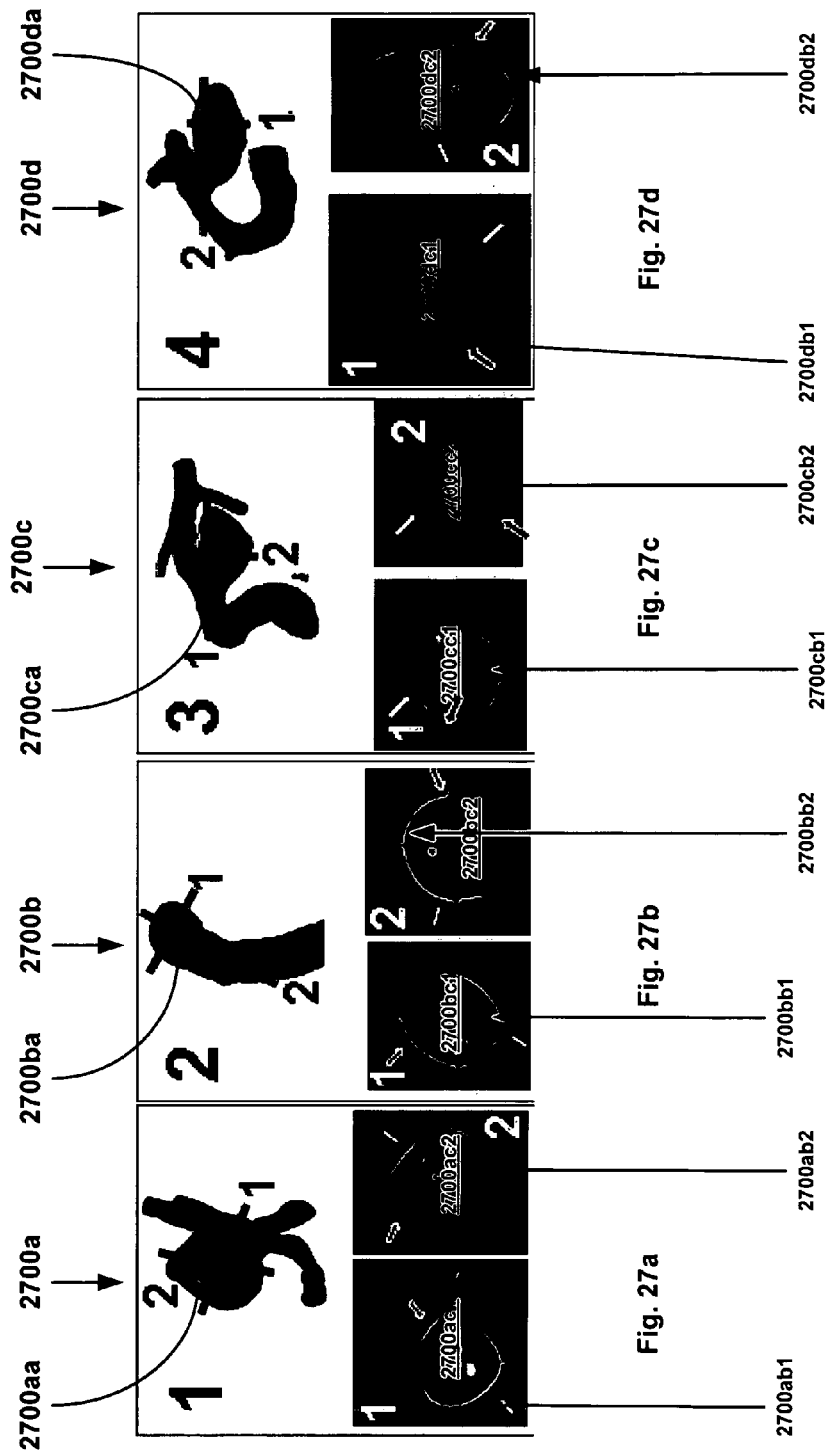

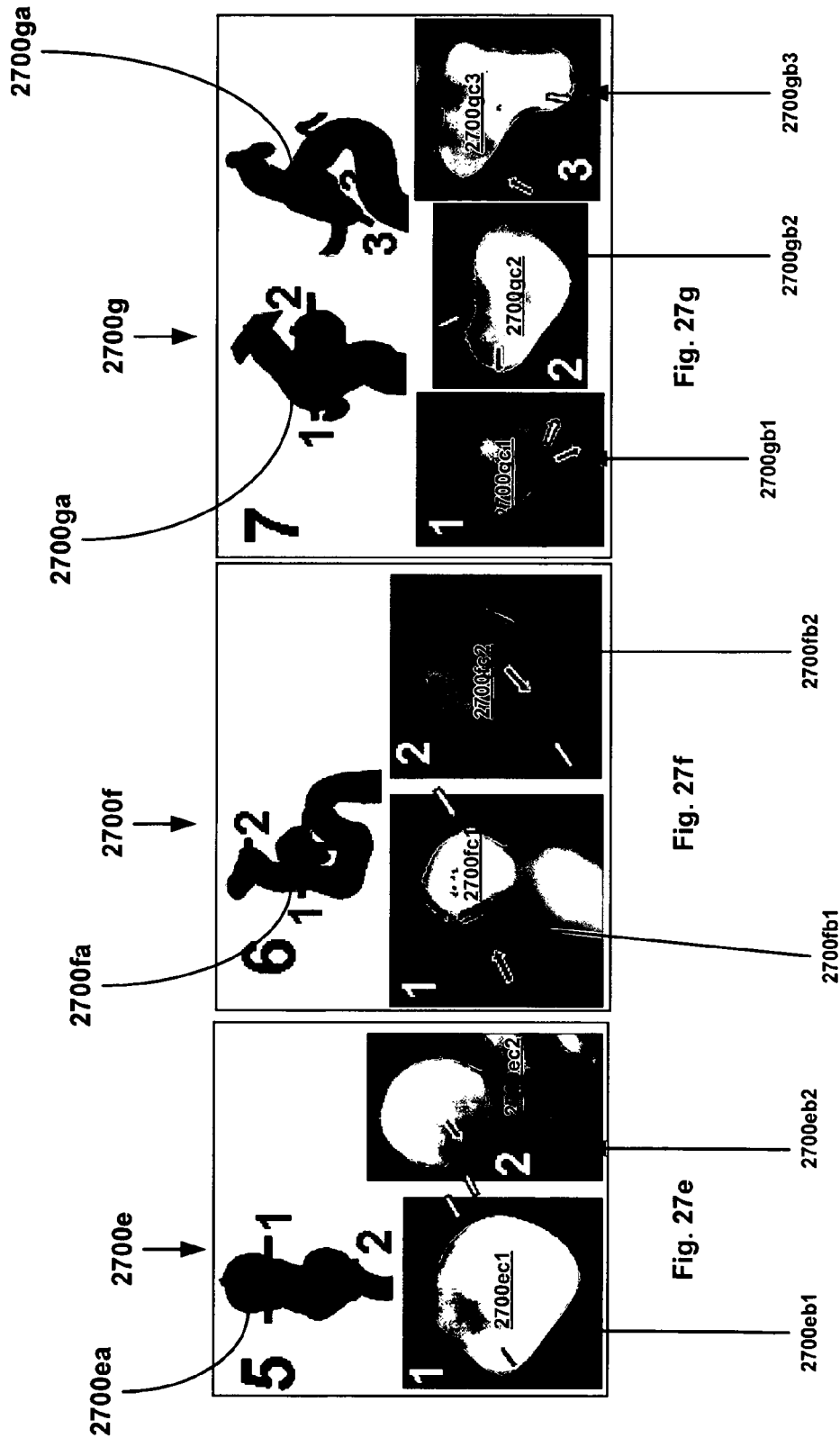

Case 1

Case 2

Case 3  Case 4

Case 5        Case 6

AUTOMATED WALL MOTION QUANTIFICATION IN AORTIC DISSECTIONS

BACKGROUND

This disclosure relates to magnetic resonance imaging systems.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 is a graphical illustration of the volumetric flow rate within the true lumen boundary of the aorta during a complete cardiac cycle.

FIG. 23 is an illustration of an exemplary experimental embodiment of the volumetric flow rate through the lumen of the proximal parent artery of an aneurysm.

FIG. 24 is an illustration of an exemplary experimental embodiment of the boundary of the lumen of an aneurysm during different time points within a complete cardiac cycle.

FIG. 25 is an illustration of an exemplary experimental embodiment of the total average displacement of the boundary of the lumen of an aneurysm during different time points within a complete cardiac cycle.

FIG. 26 is an illustration of an exemplary experimental embodiment of the calculation of the time averaged displacement of the boundary of the lumen of an aneurysm during a complete cardiac cycle.

FIG. 27a is an illustration of a vasculature, aneurysm, aneurysm MRI cross sections, and aneurysm boundaries for a subject.

FIG. 27b is an illustration of a vasculature, aneurysm, aneurysm MRI cross sections, and aneurysm boundaries for a subject.

FIG. 27c is an illustration of a vasculature, aneurysm, aneurysm MRI cross sections, and aneurysm boundaries for a subject.

FIG. 27d is an illustration of a vasculature, aneurysm, aneurysm MRI cross sections, and aneurysm boundaries for a subject.

FIG. 27e is an illustration of a vasculature, aneurysm, aneurysm MRI cross sections, and aneurysm boundaries for a subject.

FIG. 27f is an illustration of a vasculature, aneurysm, aneurysm MRI cross sections, and aneurysm boundaries for a subject.

FIG. 27g is an illustration of a vasculature, aneurysm, aneurysm MRI cross sections, and aneurysm boundaries for a subject.

DETAILED DESCRIPTION

Figure 1A:
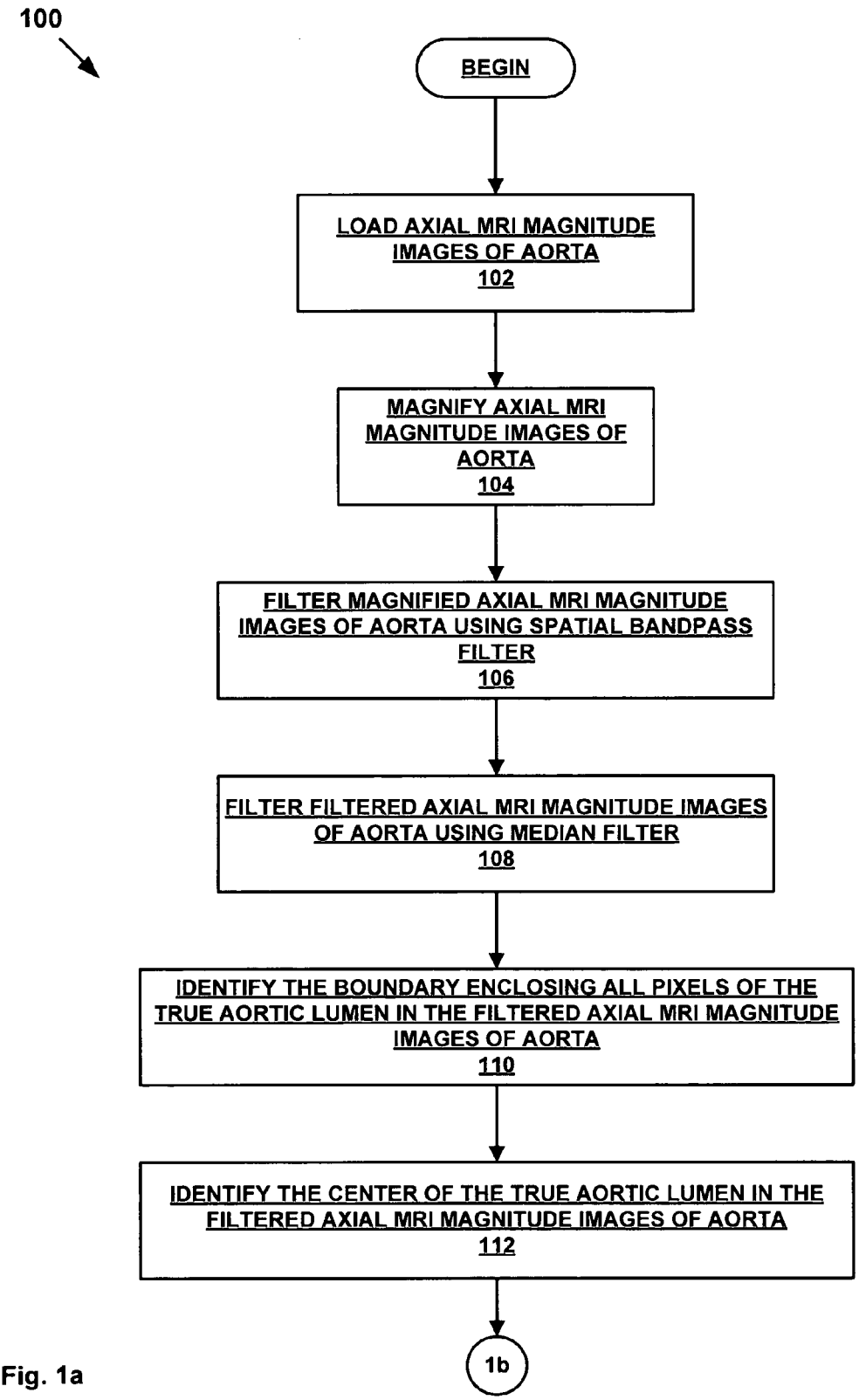
FIGS. 1a, 1b, and 1c are flow chart illustrations of an exemplary embodiment of a method of post-processing magnetic resonance images of the aorta.

In the drawings and description that follows, like parts are marked throughout the specification and drawings with the same reference numerals, respectively. The drawings are not necessarily to scale. Certain features of the invention may be shown exaggerated in scale or in somewhat schematic form and some details of conventional elements may not be shown in the interest of clarity and conciseness. The present invention is susceptible to embodiments of different forms. Specific embodiments are described in detail and are shown in the drawings, with the understanding that the present disclosure is to be considered an exemplification of the principles of the invention, and is not intended to limit the invention to that illustrated and described herein. It is to be fully recognized that the different teachings of the embodiments discussed below may be employed separately or in any suitable combination to produce desired results. The various characteristics mentioned above, as well as other features and characteristics described in more detail below, will be readily apparent to those skilled in the art upon reading the following detailed description of the embodiments, and by referring to the accompanying drawings.

Figure 1B:
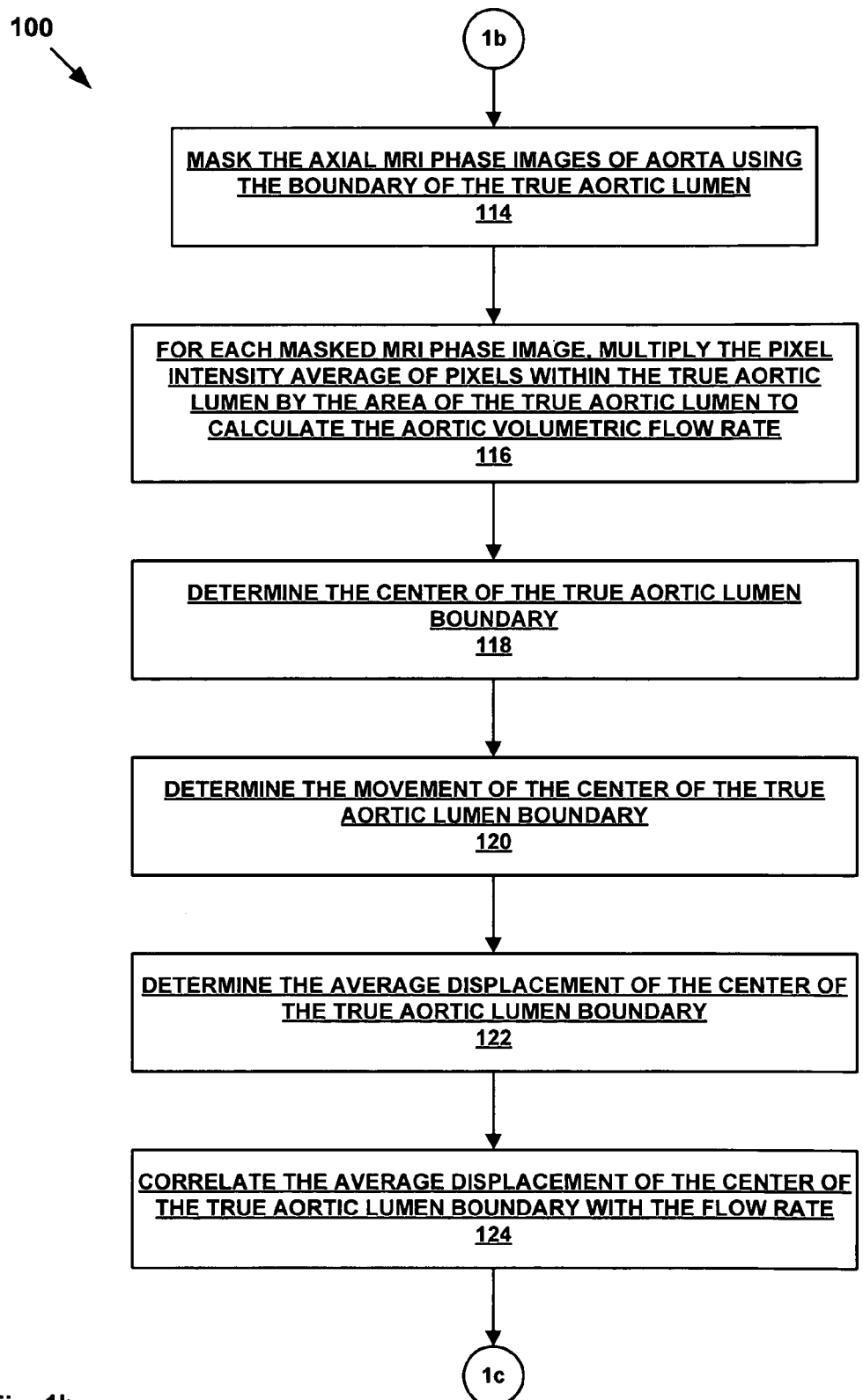
Figure 1C:
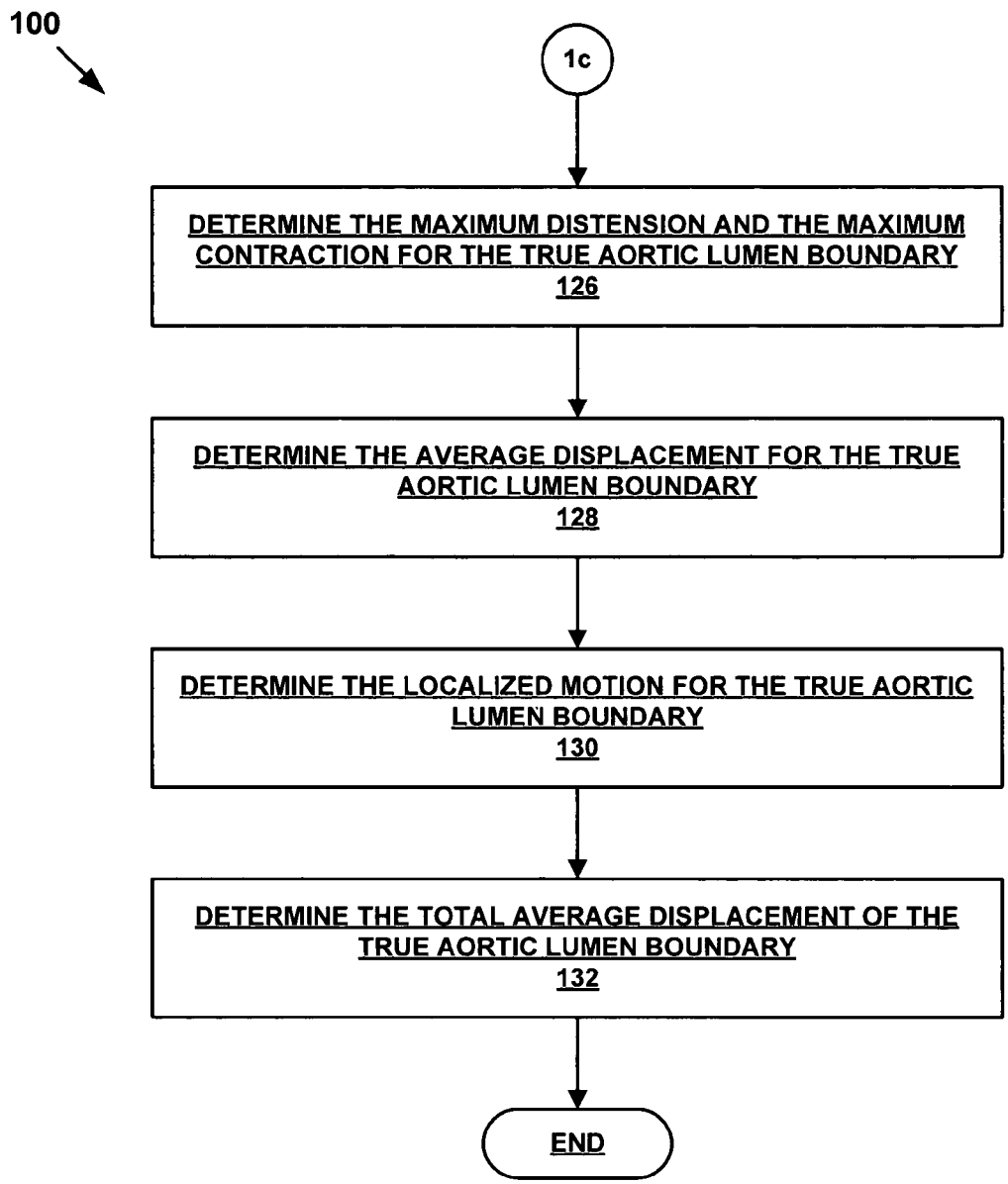
Figure 2:
FIG. 2 is an illustration of a sequence of magnetic resonance magnitude images of the aorta.

Referring to FIGS. 1a, 1b, and 1c, an exemplary embodiment of a method 100 for processing magnetic resonance imaging ("MRI") images is provided in which, in 102, a sequence 102a of MRI magnitude images of the aorta in the axial orientation, as illustrated in FIG. 2, were obtained from a subject.

The sequence 102a of MRI magnitude images are then magnified a conventional manner in 104, and then filtered in 106 using a conventional spatial bandpass filter in 106. In an exemplary embodiment, in 106, the spatial bandpass filtering eliminates image intensity variation caused by the inhomogeneous sensitivity profile of a typical MRI coil, e.g., variations larger then 80 pixels, and by noise, variations smaller than 4 pixels.

Figure 3:
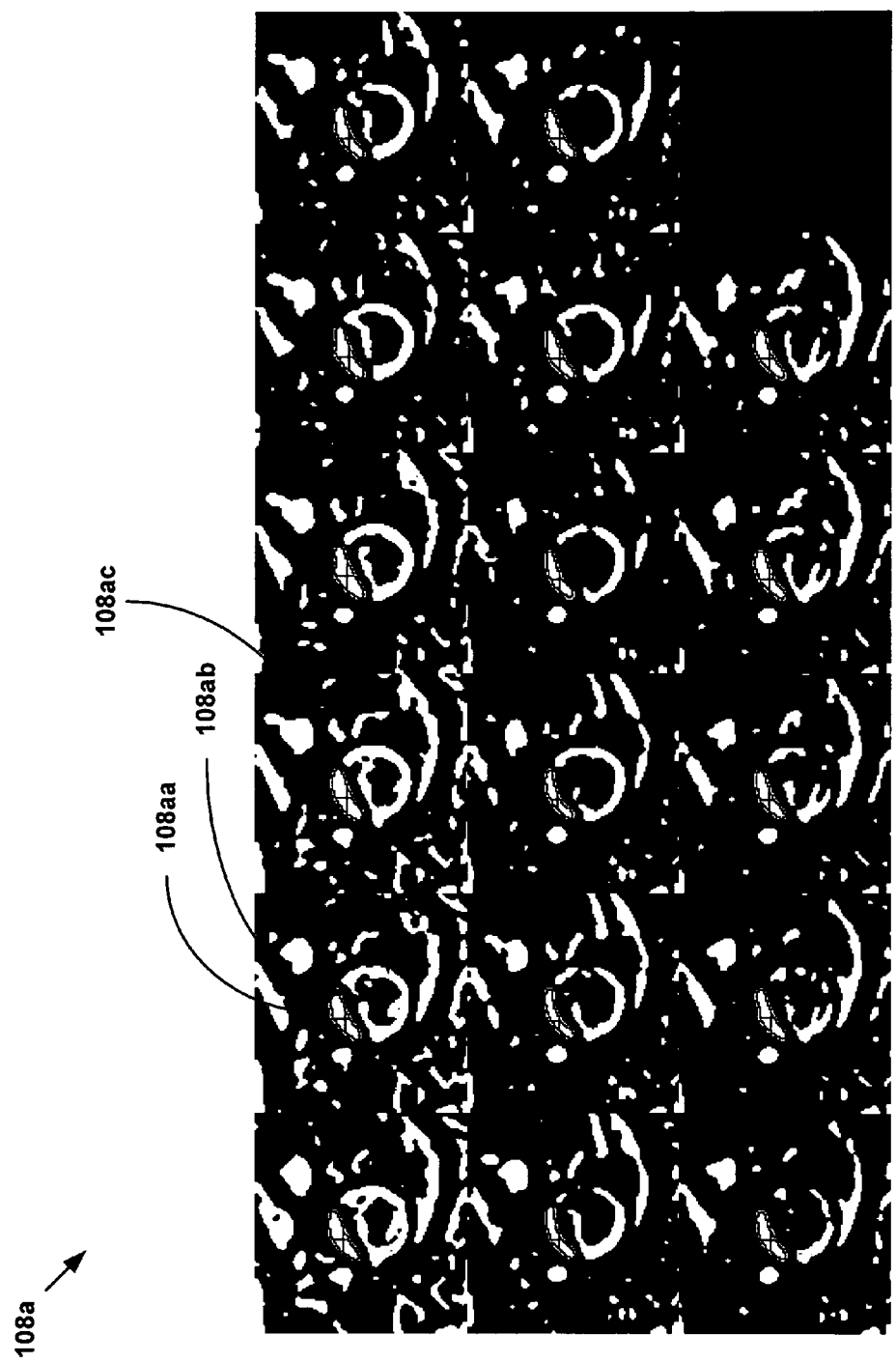
FIG. 3 is an illustration of the sequence of magnetic resonance magnitude images of the aorta of FIG. 2 after magnifying and filtering the images.

The sequence 102a of MRI magnitude images are then further filtered in 108 using a conventional median filter to generate a filtered sequence 108a of MRI magnitude images, as illustrated in FIG. 3. In an exemplary embodiment, in 108, the median filtering further reduces image intensity variations caused by noise and further homogenizes the image intensity inside the true aortic lumen. In an exemplary embodiment, in 108, the median filter also preserves edges in the MRI magnitude images. As illustrated in FIG. 3, in an exemplary embodiment, the images 108a obtained after completing 108 provide a large grayscale intensity contrast between the true aortic lumen 108aa and the aortic wall including the septum 108ab separating true and false lumen 108ac so that pixels belonging to the true aortic lumen can be segmented using conventional single value thresholding.

In an exemplary embodiment, in 104, 106, and 108, the sequence 102a of MRI magnitude images are processed using ImageJ software, version, 1.40 g, a publicly available MRI imaging post-processing software distributed by the National Institutes of Health and described at the following URL: http://rsb.info.nih.gov/ij/.

Figure 4:
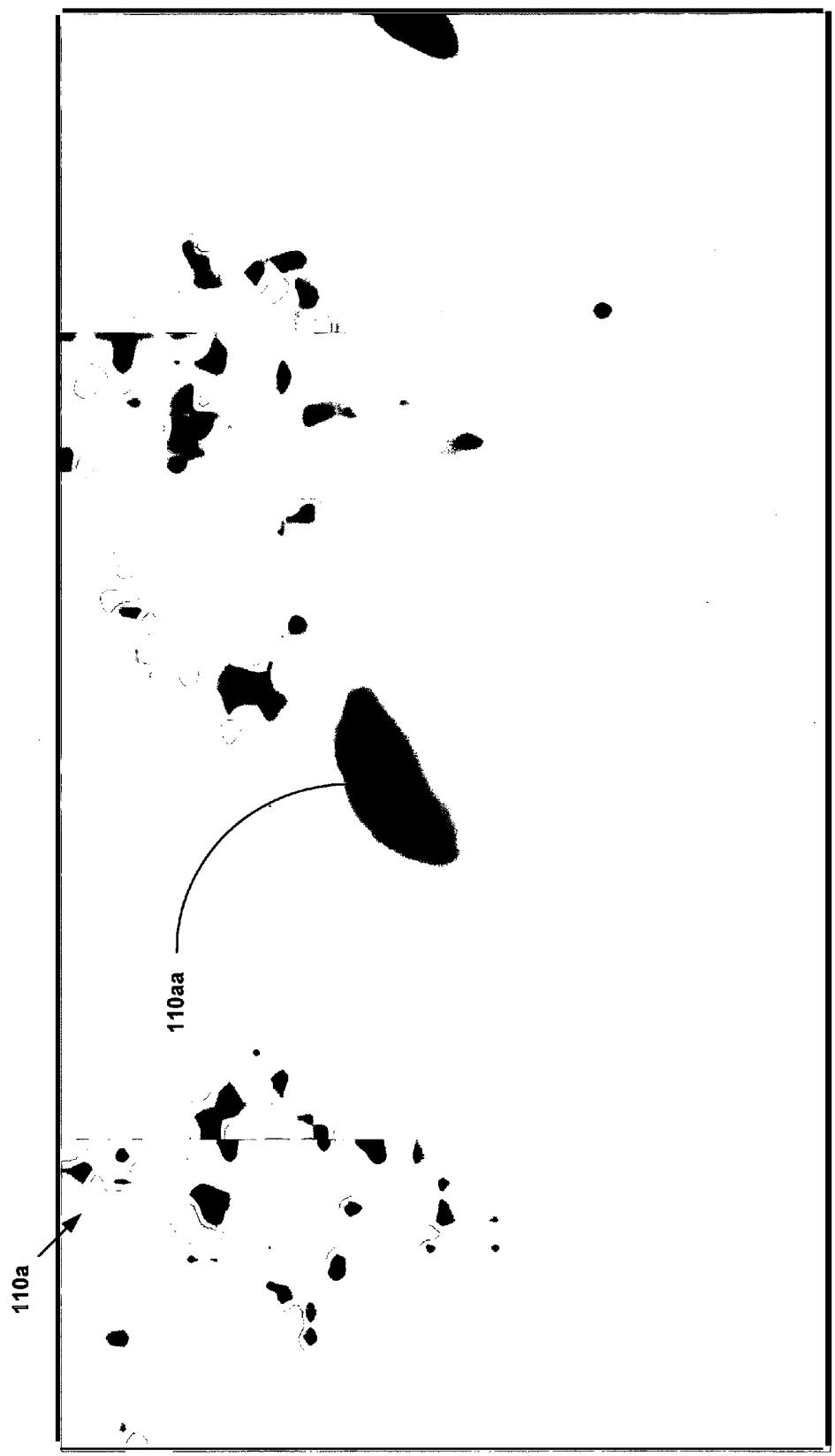
FIG. 4 is an illustration of a magnetic resonance phase image of the aorta.
Figure 5:
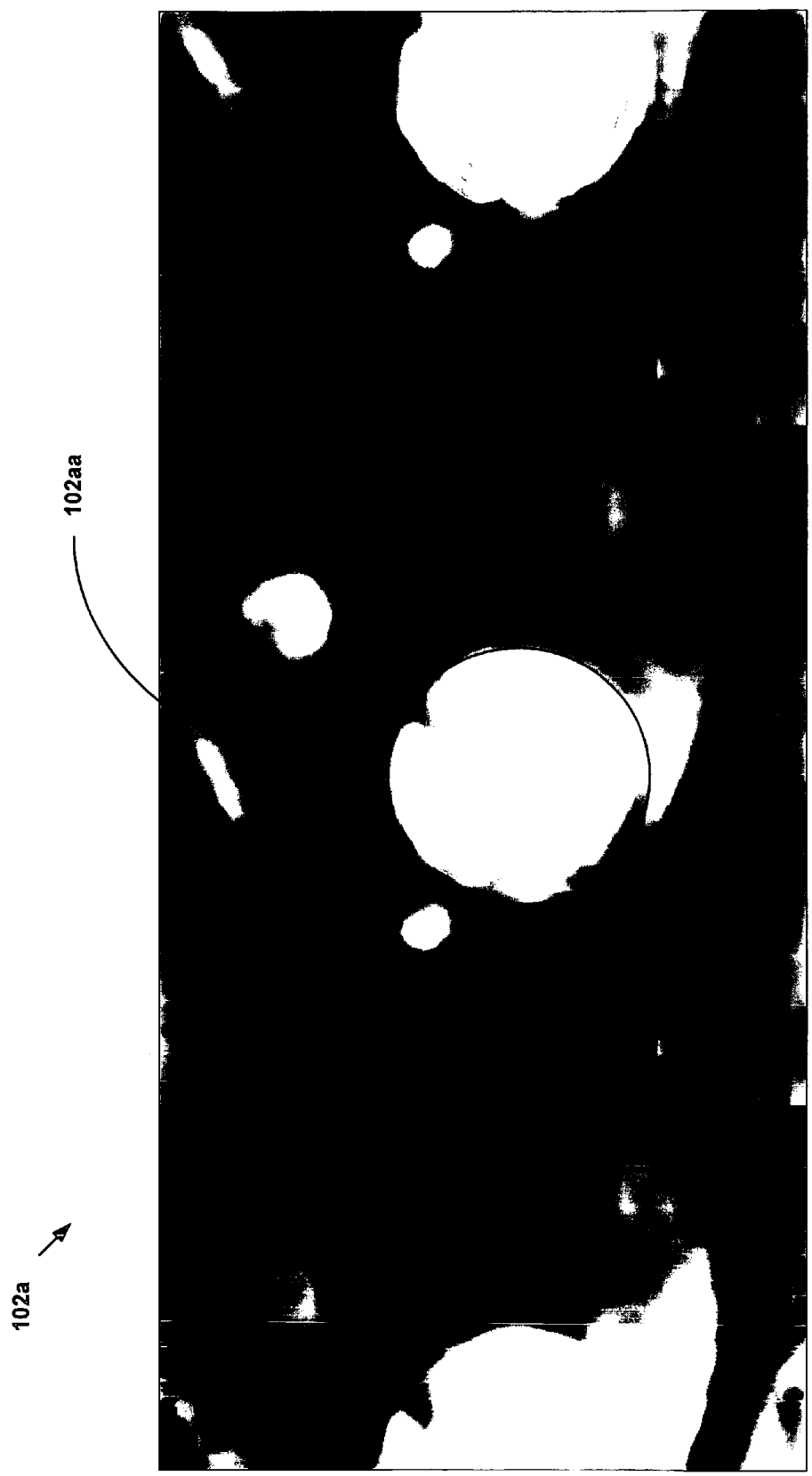
FIG. 5 is an illustration of a magnetic resonance magnitude image of the aorta illustrated in FIG. 4.

In 110, the boundary enclosing all pixels of the true aortic lumen in the images 108a is then determined. In an exemplary embodiment, in 110, as illustrated in FIGS. 4 and 5, the true aortic lumen 110aa is identified by determining the darkest contiguous structure within the corresponding phase MRI images 110a which is still contained within the cross section 102aa of the human aorta as visible in the magnitude MRI images 102a. In an exemplary embodiment, in 112, the center of the true aortic lumen is then determined using conventional mathematical methods.

Figure 6:
FIG. 6 is an illustration of the calculated boundary of the true aortic lumen for the magnetic resonance magnitude image of the aorta illustrated in FIG. 4.
Figure 7:
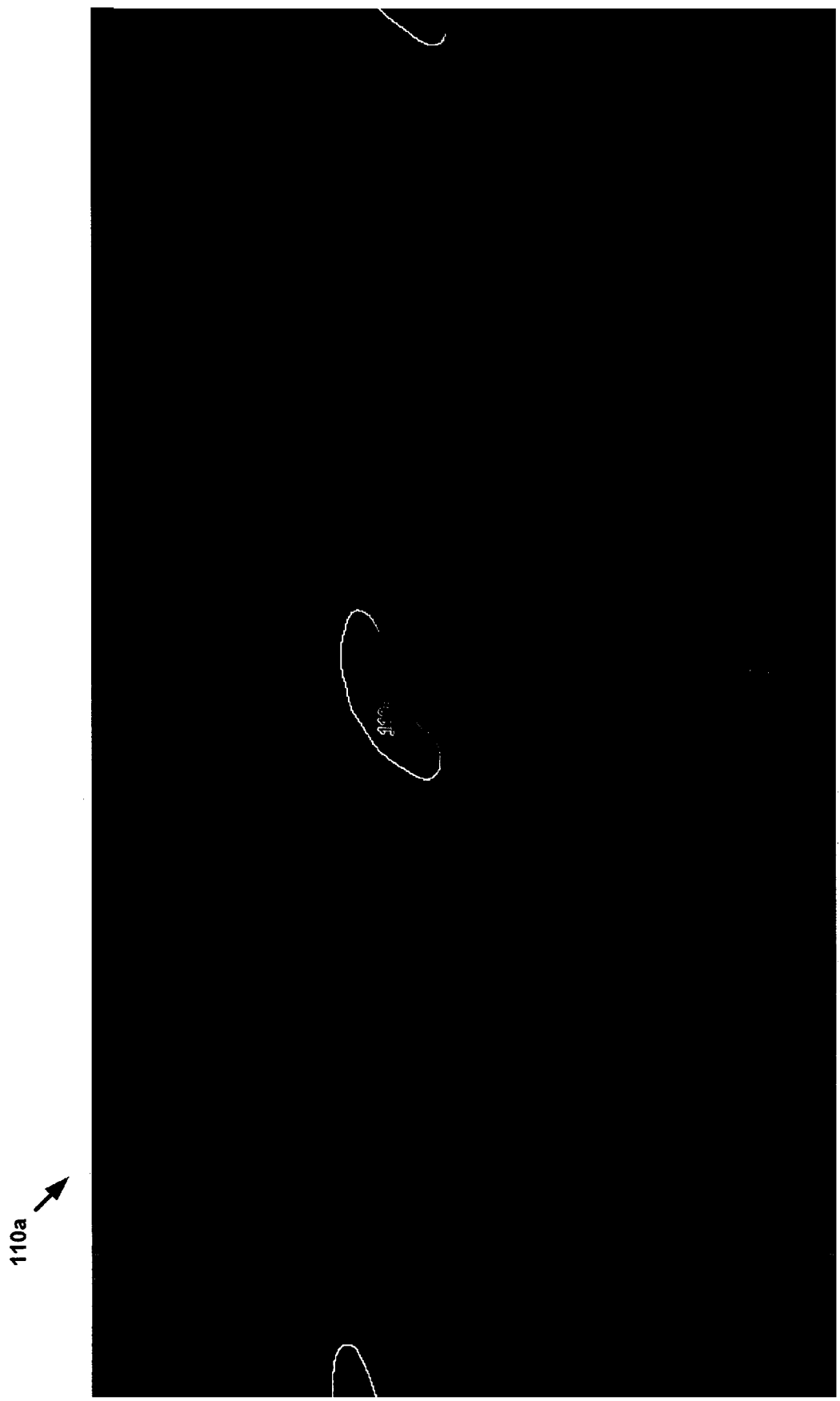
FIG. 7 is an illustration of the magnetic resonance phase image of the aorta illustrated in FIG. 4 after masking the image with the boundary of the true aortic lumen.

In 114, the corresponding phase MRI images 110a are then masked using the boundary of the true aortic lumen. In particular, as illustrated in FIG. 6, the boundary of the true aortic lumen 108d in the MRI magnitude images 108a is then used to mask the corresponding phase MRI images 110a. As a result, as illustrated in FIG. 7, the true aortic lumen 110aa is isolated in each of the phase images 110a.

In an exemplary embodiment, in 110, 112, and 114, the magnitude MRI images 108a are used to mask the corresponding phase MRI images 110a. Then, the pixel within each of the masked phase MRI images 110a with the lowest intensity is identified by Iterating through all gray scale pixel values of the masked phase MRI images. The pixel with the lowest intensity within each of the masked phase MRI images 110a then serves as a seed point for a conventional region growing algorithm and the boundary enclosing all pixels of the true aortic lumen 110aa was then found using a conventional region growing algorithm such, for example, that provided in the publicly available ImageJ software, version, 1.40 g, a publicly available MRI imaging post-processing software distributed by the National Institutes of Health and described at the following URL: http://rsb.info.nih.gov/ij/. In an exemplary embodiment, the center of the true aortic lumen 110aa is then found in 112 by determining the center of mass of all pixels belonging to the true aortic lumen in a conventional manner.

In 116, the volumetric flow rate 116a within the true aortic lumen 110aa is then determined for a complete cardiac cycle as illustrated in FIG. 8. As illustrated in FIG. 8a, the complete cardiac cycle includes systolic flow 116aa, backflow 116ab, and diastolic flow 116ac. In an exemplary embodiment, in 116, the volumetric flow rate 116a within the true aortic lumen 110aa for a complete cardiac cycle is determined by, for each true aortic lumen within the sequence of phase MRI images 110a within the cardiac cycle, multiplying the pixel intensity average of all pixels inside the true aortic lumen by the area of the true aortic lumen for each image. Since the image intensity within the true aortic lumen 110aa of the phase MRI images 110a is proportional to the velocity of the blood flow therein, the product of the pixel intensity average within and the cross sectional area of the true aortic lumen 110aa is the aortic volumetric flow rate.

Figure 9:
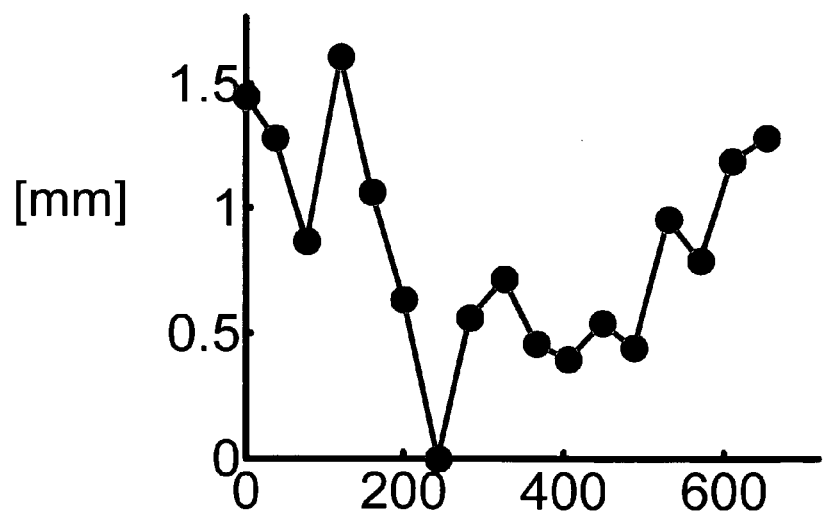
FIG. 9 is a graphical illustration of the motion of the center of the true lumen boundary of the aorta.

In 118, the center of the boundary of the true aortic lumen ("ALC") is then determined by calculating the center of mass of the lumen boundary points around the periphery of the true aortic lumen 110aa. In 120, as illustrated in FIG. 9, the displacement 120a of the ALC is measured for each time point in the cardiac cycle relative to the time of minimal inflow. In 122, the average maximum displacement of the ALC is calculated for all cross sections and for all time points within the cardiac cycle as an approximation for the global motion of the entire aorta. In 124, the time-dependence of the ALC displacement is correlated with the inflow waveform using the Pearson correlation coefficient $r_{ALC}$.

Figure 10:
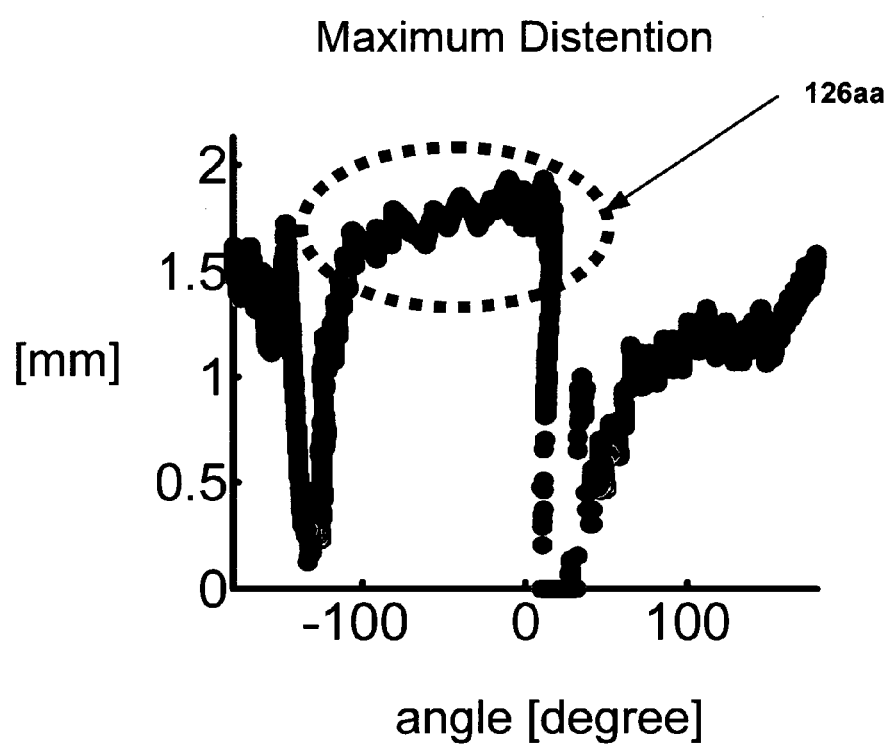
FIG. 10 is a graphical illustration of the maximum distension of the true lumen boundary of the aorta.
Figure 11:
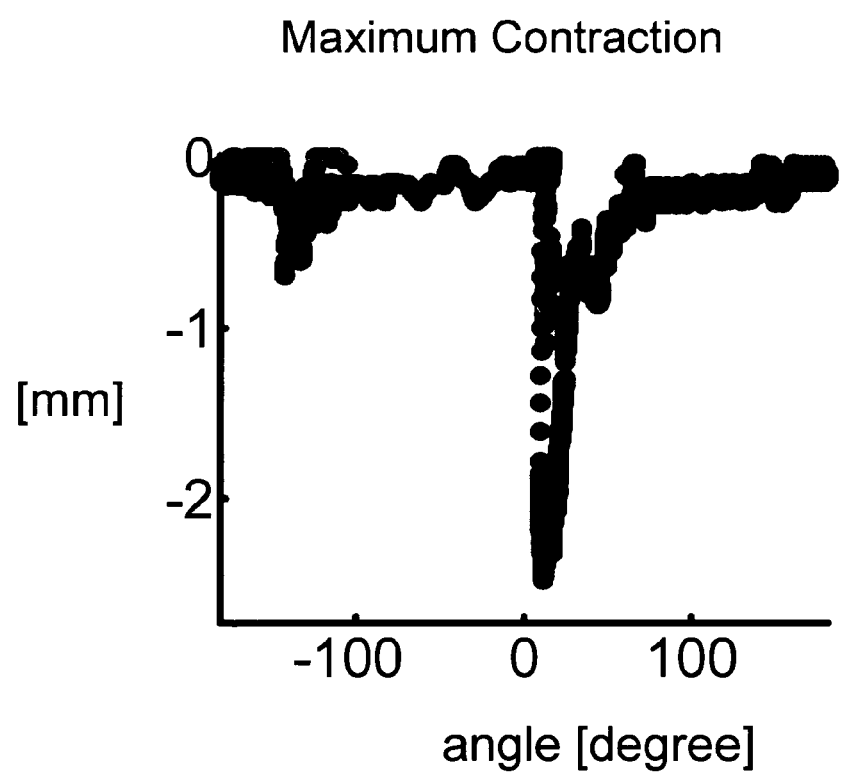
FIG. 11 is a graphical illustration of the maximum contraction of the true lumen boundary of the aorta.

In an exemplary embodiment, in 126, as illustrated in FIGS. 10 and 11, the maximum distension 126a and the maximum contraction 126b for all of the boundary points of the true aortic lumen 110aa within a cardiac cycle are determined. In an exemplary embodiment, the intraluminal septum of the true aortic lumen 110aa includes a maximum distension 126aa.

In an exemplary embodiment, in 126, with the ALC as an origin, a 2D polar coordinate system is defined within the true aortic lumen 110aa for each time point thus excluding the motion of ALC. Each boundary point on the true aortic lumen 110aa is then characterized by a radial coordinate r and an angular coordinate, an azimuth angle a. Displacement $d_i(t)$ for each boundary point i perpendicular to the boundary of the true aortic lumen 110aa is then calculated as the difference of $r_i(t)$ and of $r_0$ at the time of minimal inflow: $d_i(t)=r_i(t)-r_0$. Maximum distension, 126a or $d_{max}$, positive, and maximum contraction, 126b or $d_{min}$, negative, for all n boundary points is defined as the maximum, or minimum, respectively, of all displacements for all boundary points and for all times t within a cardiac cycle as follows:

$$d_{max} = \max_{\substack{t \in cardiaccycle \\ i=1,\ldots,n}} \{d_i(t)\}$$

$$d_{min} = \min_{\substack{t \in cardiaccycle \\ i=1,\ldots,n}} \{d_i(t)\}.$$

Figure 12:
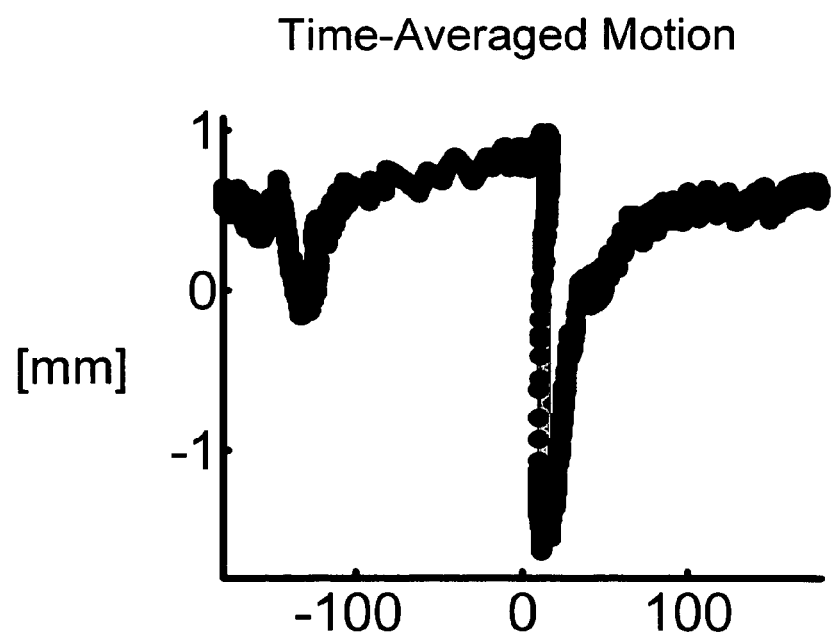
FIG. 12 is a graphical illustration of the average displacement of the true lumen boundary of the aorta.

In an exemplary embodiment, in 128, as illustrated in FIG. 12, the average displacement 128a for all of the boundary points of the true aortic lumen 110aa within a cardiac cycle are determined. In an exemplary embodiment, in 128, the average displacement 128a or $d_{ave,i}$ for each boundary point i is defined as a temporal average over all distances $d_i(t)$, in equation form:

$$d_{ave,i} = <d_i(t)>_{cardiaccycle}$$

In an exemplary embodiment, the mean value of $d_{ave}$ and the standard deviation $\Delta d_{ave}$ as a measure of variation in the time-averaged displacement is determined for all boundary points for each cross section of the true aortic lumen 110aa.

In an exemplary embodiment, in 130, the localized motion of the boundary of the true aortic lumen 110aa is determined. In an exemplary embodiment, the localized motion of the true aortic lumen 110aa provides a measure of the inhomogeneity of the aortic motion. In an exemplary embodiment, in 130, in determining the localized motion of the boundary of the true aortic lumen 110aa, $d_i(t)$ is correlated with the inflow waveform. Then, in an exemplary embodiment, the ratio of the number of positive ($r_{pos}$) and negative ($r_{neg}$) significant correlations (p-value$\leq$0.05) relative to the total number of boundary points in the true aortic lumen 110aa is calculated to determine what fraction of the boundary of the true aortic lumen moves in phase ($r_{pos}$) and what fraction moves out-of-phase ($r_{neg}$) relative to the inflow waveform during a cardiac cycle. In an exemplary embodiment, the difference angle of the angles of maximum distension ($a_{max}$) and maximum contraction ($a_{min}$)$\Delta a = a_{max} - a_{min}$ are determined to characterize the locations of the maximal distension and maximal contraction relative to each other.

Figure 13:
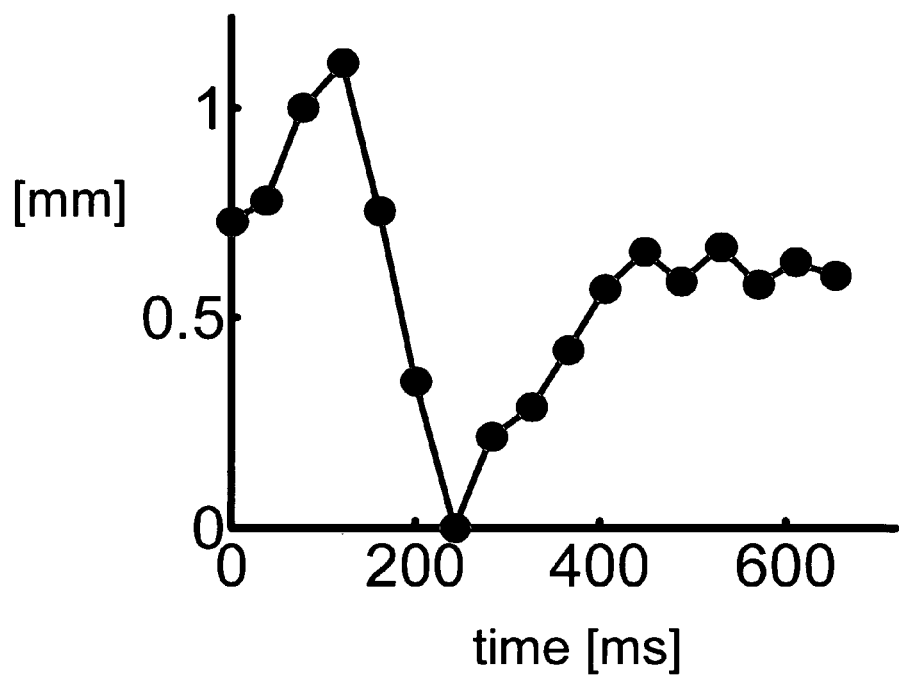
FIG. 13 is a graphical illustration of the time averaged motion of the true lumen boundary of the aorta.

In an exemplary embodiment, in 132, as illustrated in FIG. 13, the total average displacement 132a for all points in the boundary of the true aortic lumen 110aa is determined.

In an exemplary embodiment, in 132, the total average displacement 132a, or AD(t), quantifies the total aortic lumen boundary motion at each time point during a cardiac cycle. In an exemplary embodiment, the total average displacement 132a, or AD(t), is defined as the displacement averaged over all time points for each boundary point as follows:

$$AD(t) = \operatorname*{avg}_{i=1,\ldots,n} <d_i(t)>_{boundary}$$

In an exemplary embodiment, the correlation $r_{AD(t)}$ of the time-dependent quantity AD(t) with the volumetric inflow waveform is determined with the Pearson correlation coefficient (statistical significance with a p-value<0.05).

In an exemplary experimental embodiment, the method 100 was implemented on MRI images for a subject and yielded the following results:

| Calculated Parameter | | | | | | | | | | | |
|---|---|---|---|---|---|---|---|---|---|---|---|
| $d_{max}$ | $d_{min}$ | $d_{ave}$ | $\Delta d_{ave}$ | $r_{pos}$ | $r_{neg}$ | $r_{AD(t)}$ | $p_{AD(t)}$ | $r_{ALC}$ | $p_{ALC}$ | $a_{max}$ | $a_{min}$ |
| 1.94 | −2.48 | 0.54 | 0.38 | 0.21 | 0.08 | −0.23 | 0.37 | −0.22 | 0.39 | −10 | 11 |

In an exemplary embodiment, the teachings of the present exemplary embodiments may be employed as a diagnostic tool for detecting, monitoring, and predicting disease processes in patients such as, for example, aortic dissections, cerebral aneurysms, and other arterial and vascular medical conditions.

The majority of the conventional morphological risk factors for cerebral aneurismal growth and rupture, including size, aspect-ratio, aneurysm ostium area to aneurysm volume, or aneurysm neck angle, are mostly static. Such conventional morphological risk factors for aneurismal growth and rupture do no take into account temporal changes that occur during a cardiac cycle. These conventional risk factors are either derived from time-averaged image data, such as 3D digital subtraction angiography ("DSA") or 3D time-of-flight ("TOF") magnetic resonance imaging ("MRI"), or from 2D projection DSA images acquired only during one time point in the cardiac cycle. Also, mostly static 3D image data, in particular, 3D DSA images, are conventionally used to simulate the hemodynamics in cerebral aneurysms to explore the potential of parameters such as wall shear stresses ("WSS") and dynamic pressures as possible predictors for aneurysm growth or rupture.

The pulsatility of cerebral aneurysms of relatively large amplitude is also known in the art. Furthermore, localized variations of stiffness in the aneurysmal wall have been revealed by known experimental tests which are most likely caused by the varying amount of smooth muscle and extra cellular matrix components, primary collagen fibers. A known theoretical investigation has also recently linked local variations in wall thickness and material stiffness to local stress concentrations and changes in aneurysmal shape. The inhomogeneous distribution of the material properties across the aneurysmal wall may translate into a spatially inhomogeneous aneurysmal wall motion when exposed to varying dynamic pressures during the cardiac cycle. Furthermore, theoretical models for aneurysmal wall motion for the purpose of understanding its potential influence on aneurysm rupture have been proposed that have included models consisting of linear and non-linear versions of Laplace's law and more recent approaches employ more advanced models.

In view of the drawbacks of the conventional approaches for detecting, monitoring, and predicting aneurismal growth and rupture, a fast, readily available, non-invasive in-vivo measurement technique that is capable of quantifying local aneurysm wall motion would be very valuable to 1) provide a method for identifying wall regions of high mobility, 2) for estimating the impact on computational fluid dynamics ("CFD") simulations performed with static morphological 3D images, 3) for providing more accurate boundary conditions for CFD simulations other than the now widely used static or rigid walls and 4) as a means to validate and to improve theoretical models that predict aneurysmal wall displacement derived from first principles.

Figure 14:
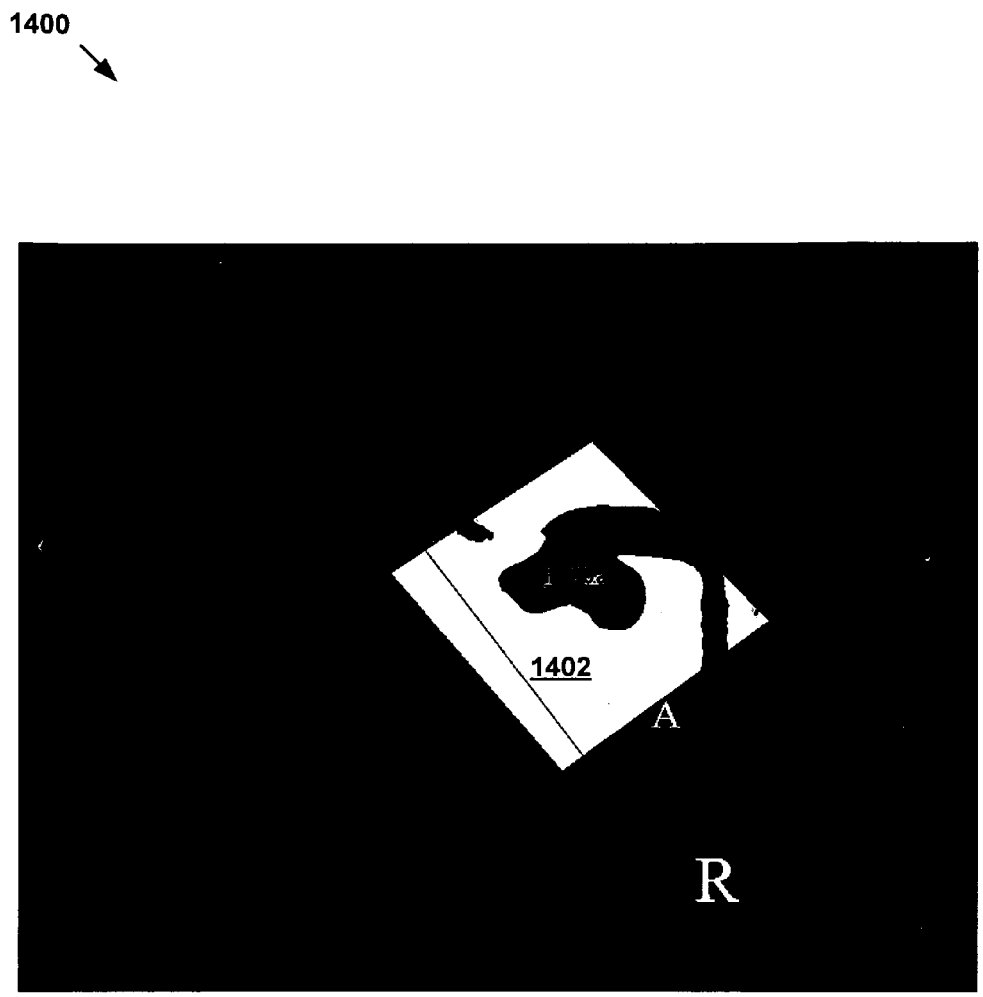
FIG. 14 is an illustration of an exemplary embodiment of a cerebral vasculature including an aneurysm.

Referring to FIG. 14, a 3D surface reconstruction of an exemplary experimental cerebral vasculature 1400 for a subject includes a prescribed intra-aneurysmal cross section 1402 that cuts through a cross section of the aneurysm 1400a.

Figure 15A:
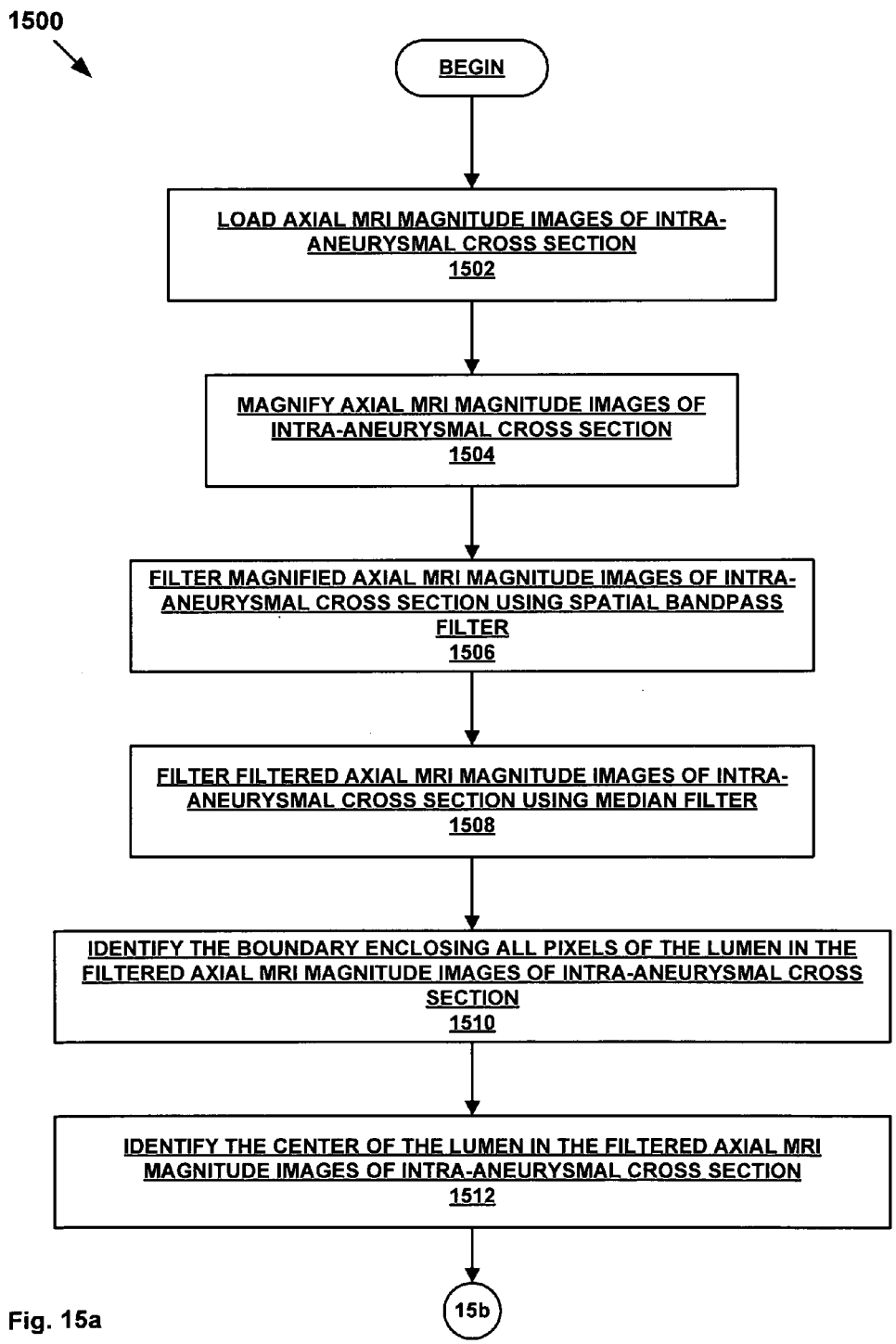
FIGS. 15a, 15b, and 15c are flow chart illustrations of an exemplary embodiment of a method of post-processing magnetic resonance images of an aneurysm.
Figure 15B:
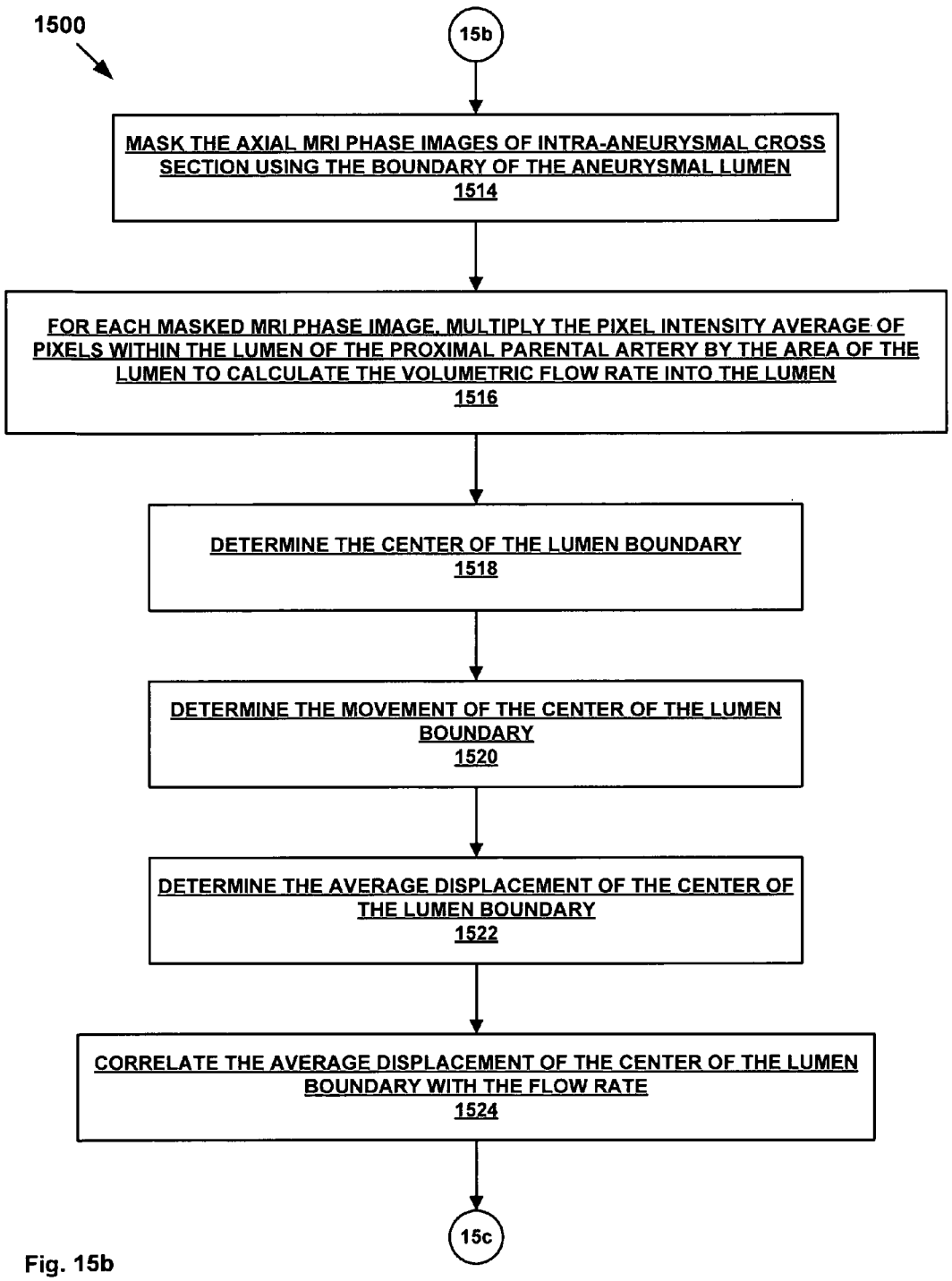
Figure 15C:
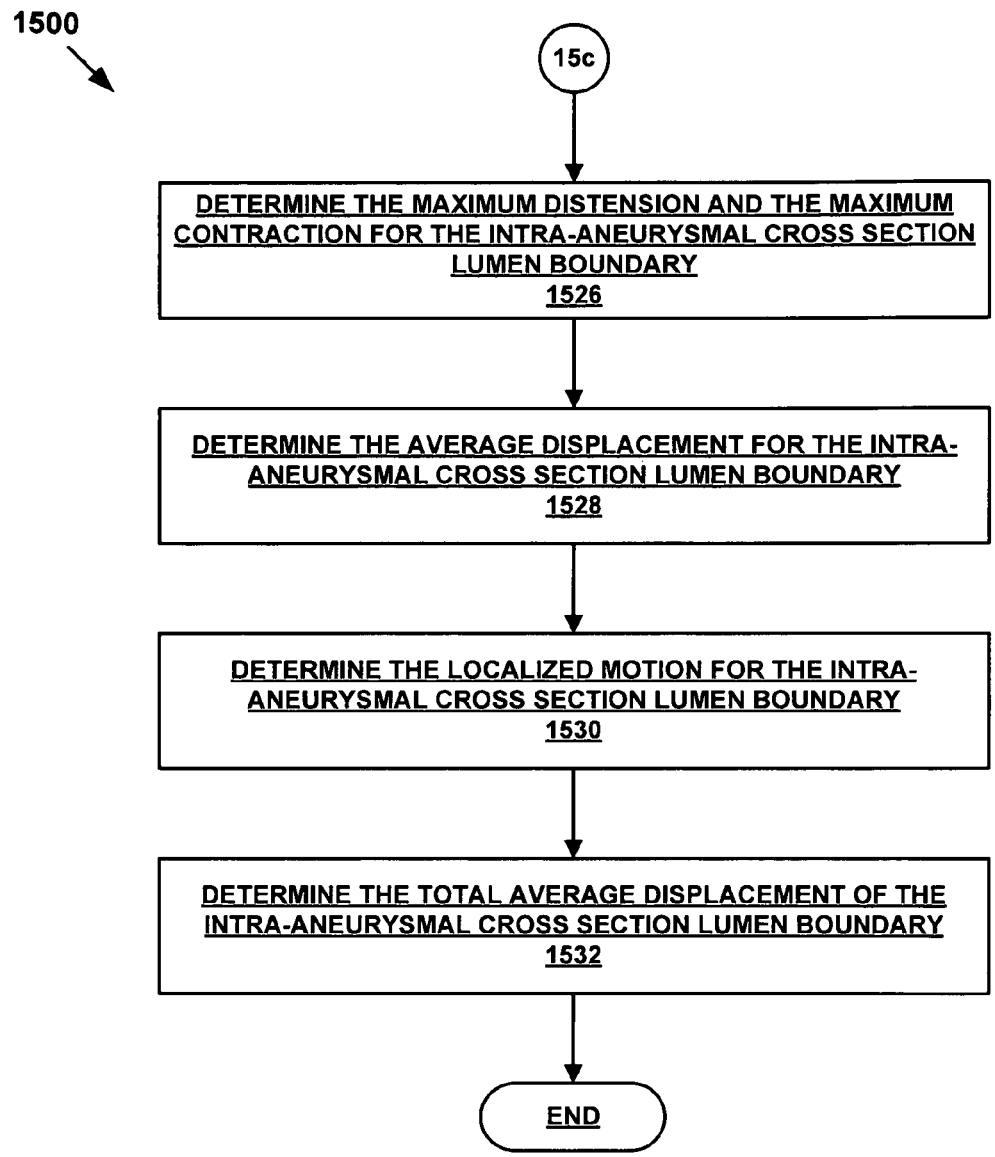

Referring to FIGS. 15a, 15b, and 15C, an exemplary embodiment of a method 1500 for detecting, monitoring, and predicting aneurismal growth and rupture is substantially identical to the method 100 except that the lumen and the lumen boundary of the intra-aneurysmal cross section 1402 of the aneurysm 1400a is detected, monitored and characterized and the volumetric flow rate is not determined from the lumen of the aneurysm but from a lumen of the cross section of the proximal parent artery in the same fashion as the aortic volumetric flow rate. Consequently, the operation of the steps 1502, 1504, 1506, 1508, 1510, 1512, 1514, 1516, 1518, 1520, 1522, 1524, 1526, 1528, 1530, and 1532 of the method 1500 are substantially identical to the operation of the steps 102, 104, 106, 108, 110, 112, 114, 116, 118, 120, 122, 124, 126, 128, 130, and 132, respectively, of the method 100 except that the lumen and the lumen boundary of the intra-aneurysmal cross section 1402 of the aneurysm 1400a is detected, monitored and characterized.

Figure 16:
FIG. 16 is an illustration of an exemplary experimental embodiment of an MRI magnitude image of an aneurysm.

Referring to FIG. 16, in an exemplary experimental implementation of the method 1500, after completing 1504, an exemplary MRI magnitude image 1504a was generated.

Figure 17:
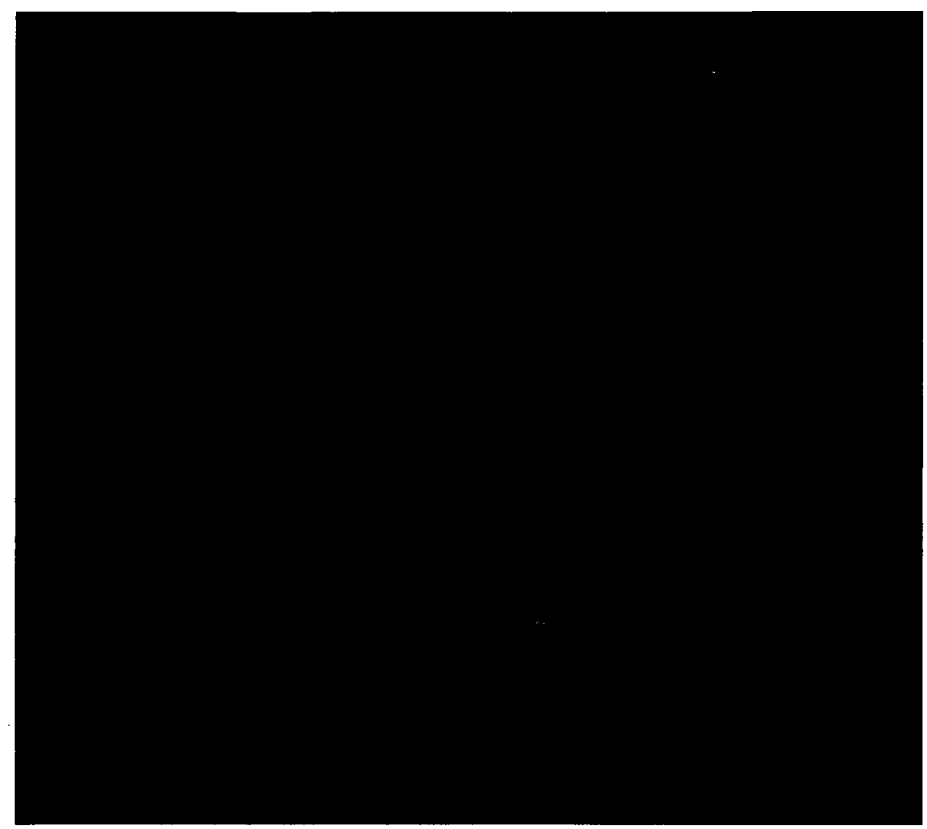
FIG. 17 is an illustration of an exemplary experimental embodiment of the MRI magnitude image of FIG. 16.

Referring to FIG. 17, in an exemplary experimental implementation of the method 1500, after completing 1506, an exemplary MRI magnitude image 1506a was generated.

Figure 18:
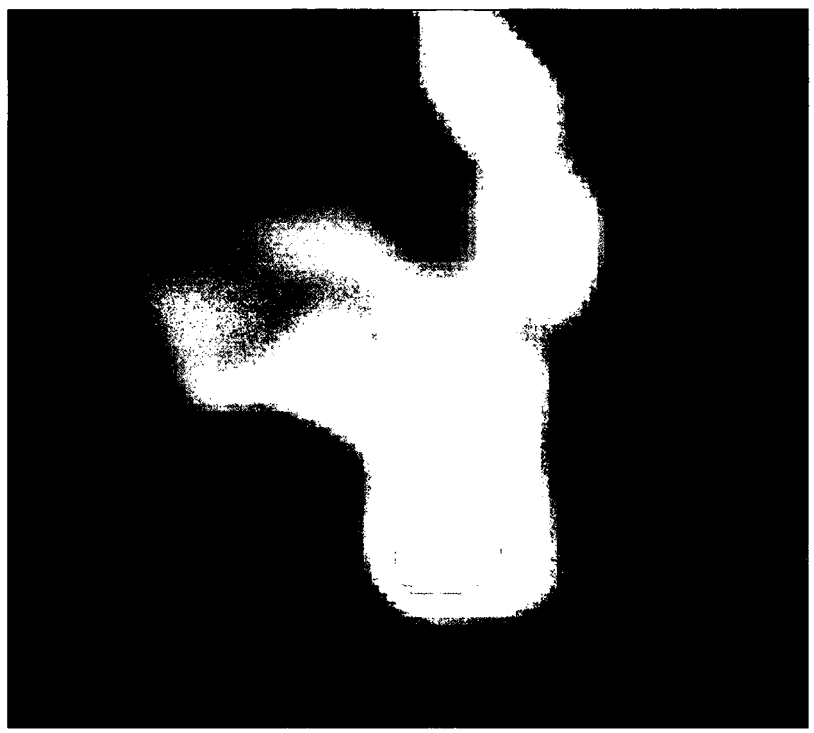
FIG. 18 is an illustration of an exemplary experimental embodiment of the MRI magnitude image of FIG. 17 after further filtering the image of an aneurysm.

Referring to FIG. 18, in an exemplary experimental implementation of the method 1500, after completing 1508, an exemplary MRI magnitude image 1508a was generated.

Figure 19:
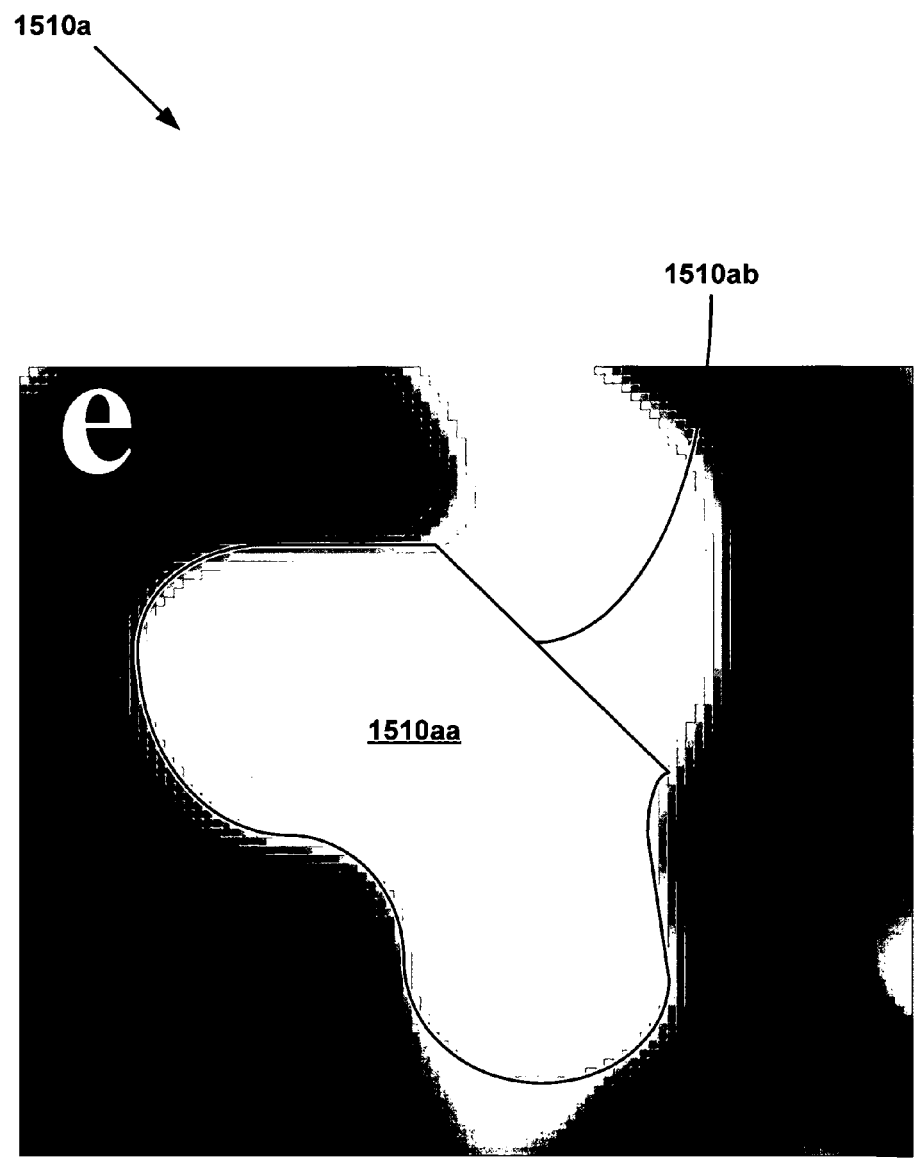
FIG. 19 is an illustration of an exemplary experimental embodiment of the MRI magnitude image of FIG. 18 after processing the image to generate the lumen boundary of an aneurysm.

Referring to FIG. 19, in an exemplary experimental implementation of the method 1500, after completing 1510, an exemplary MRI magnitude image 1510a was generated that includes the lumen 1510aa and lumen boundary 1510ab of the aneurysm.

Figure 20:
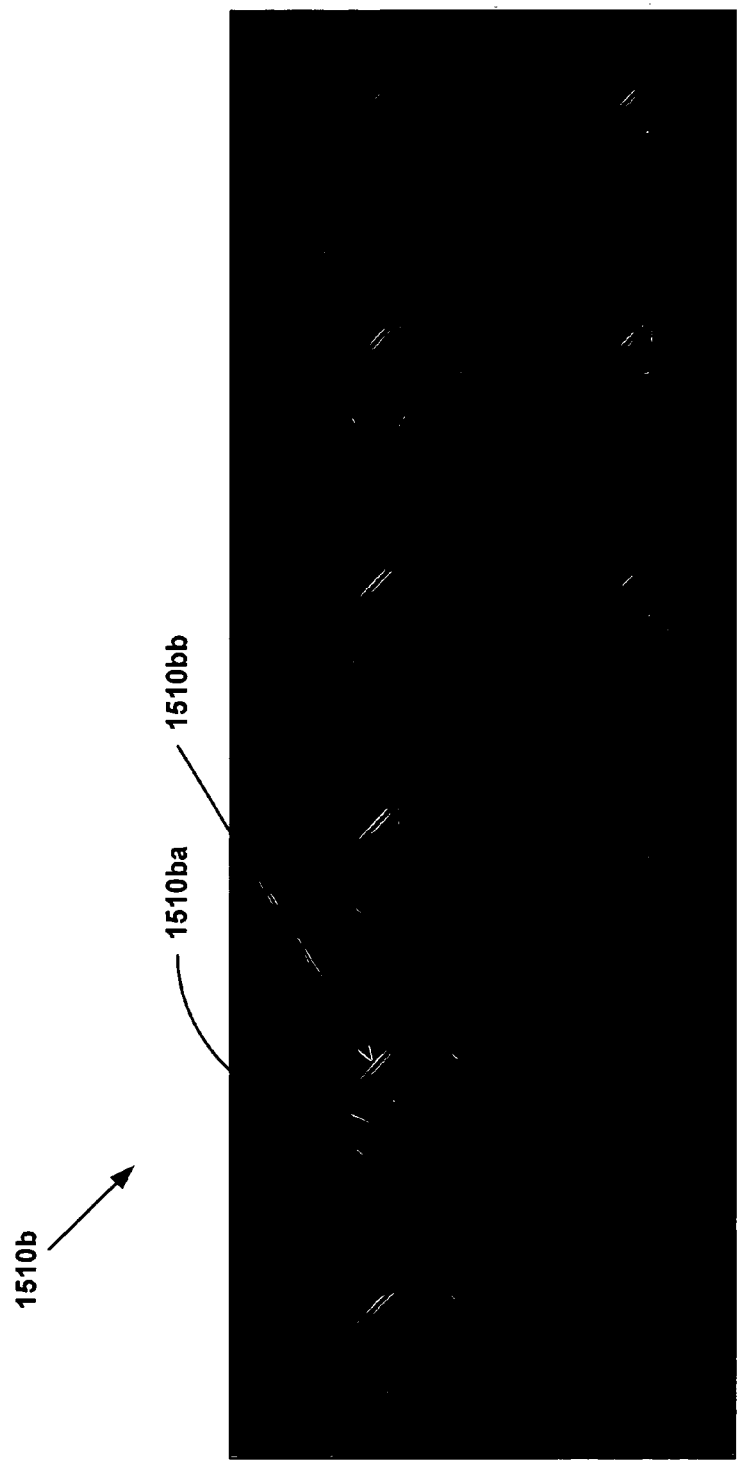
FIG. 20 is an illustration of an exemplary experimental embodiment of a sequence of MRI magnitude images after processing the images to generate the corresponding lumen boundaries at different times in the cardiac cycle of an aneurysm.

Referring to FIG. 20, in an exemplary experimental implementation of the method 1500, after completing 1510, a sequence of exemplary MRI magnitude images 1510b were generated that includes the corresponding lumen 1510ba and lumen boundary 1510bb of the aneurysm for each sequential image.

Figure 21:
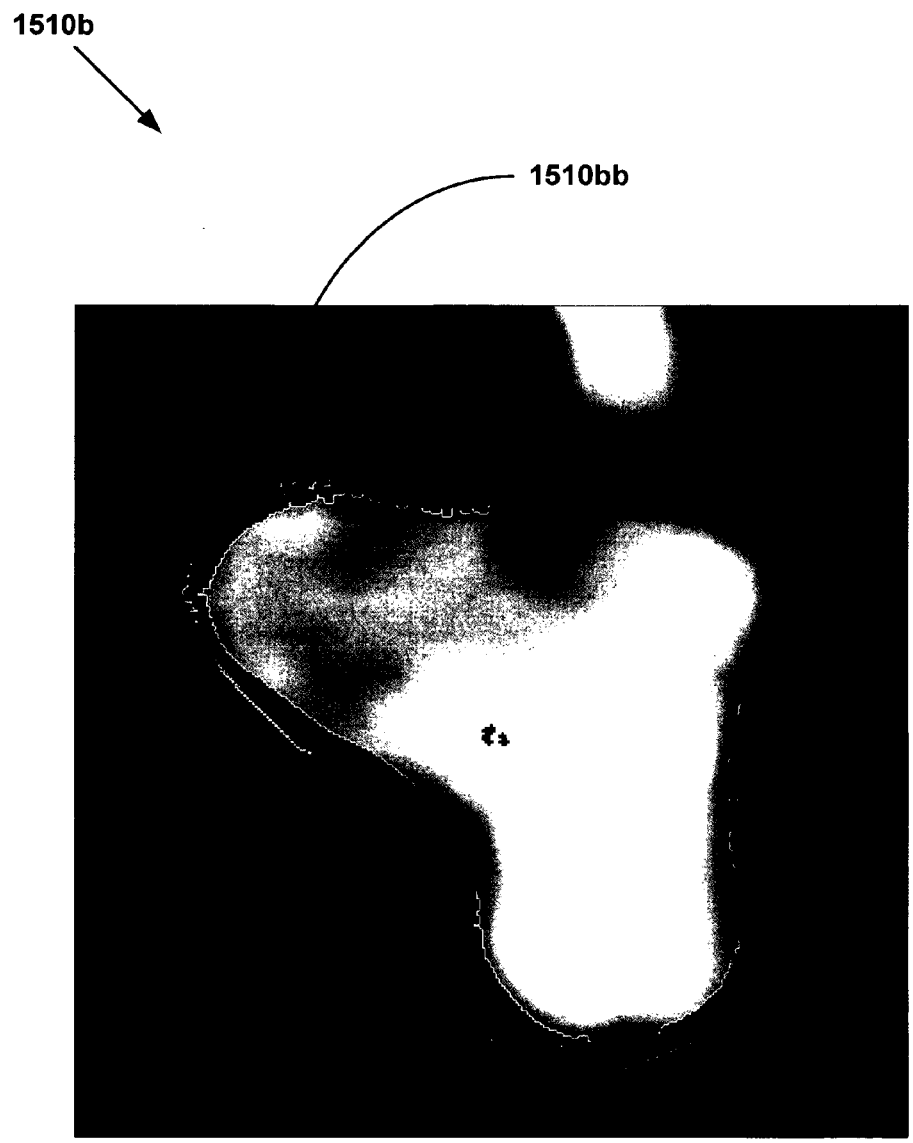
FIG. 21 is an illustration of an exemplary experimental embodiment of a time averaged MRI magnitude images with the lumen boundaries at different times in the cardiac cycle superimposed of an aneurysm.

Referring to FIG. 21, in an exemplary experimental implementation of the method 1500, after completing 1510, a sequence of color-coded lumen boundaries 1510bb of the aneurysm for each sequential image within a cardiac cycle were superimposed over an exemplary MRI magnitude image 1510b of the aneurysm.

Figure 22:
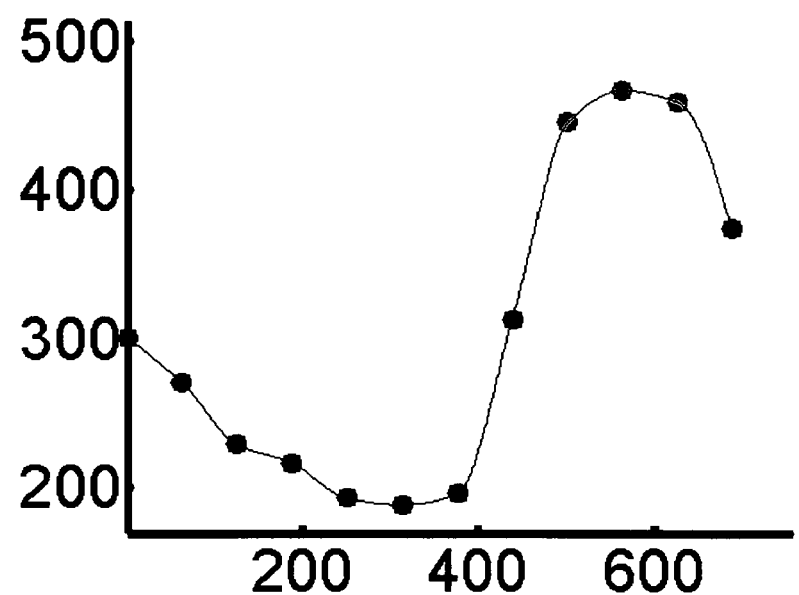
FIG. 22 is an illustration of an exemplary experimental embodiment of the volumetric flow rate through the lumen of the proximal parent artery of an aneurysm.
Figures 28A, 28B:
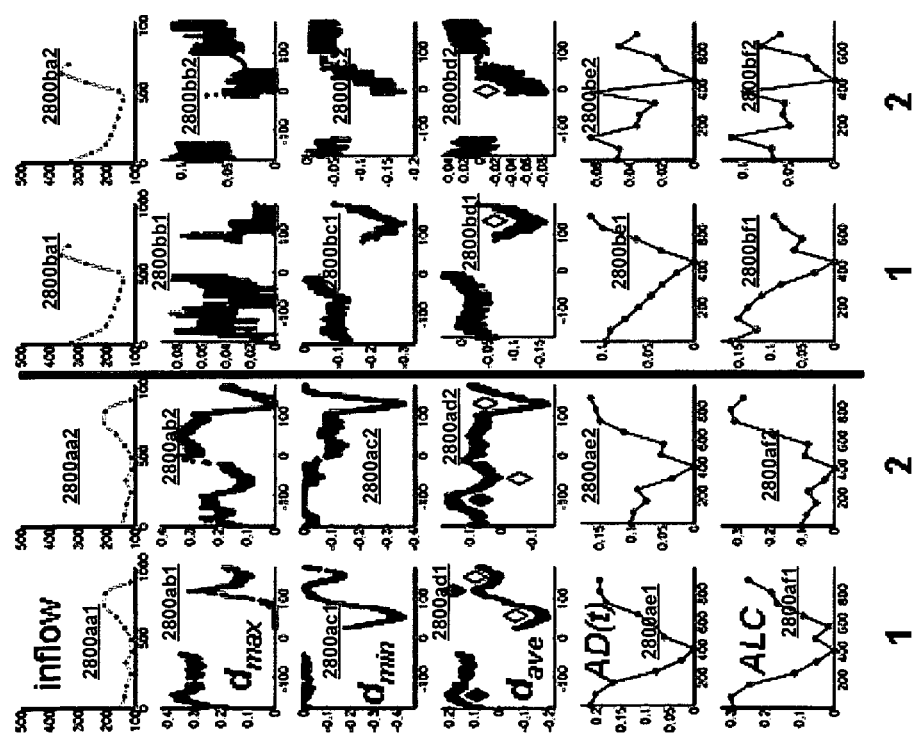
FIG. 28a is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
FIG. 28b is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
Figures 28C, 28D:
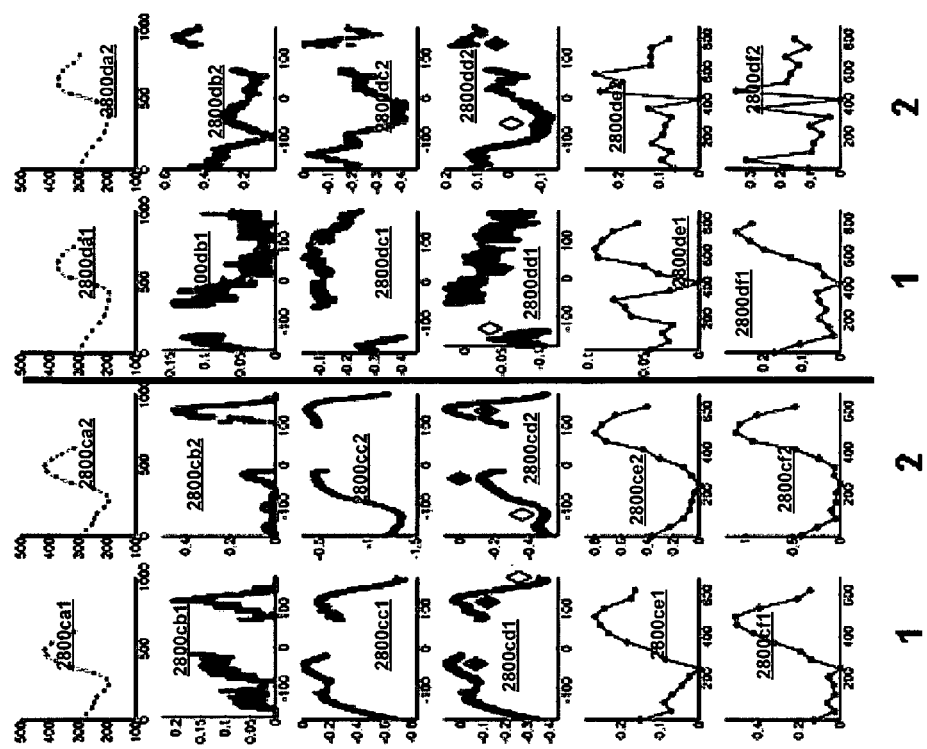
FIG. 28c is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
FIG. 28d is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
Figures 28E, 28F:
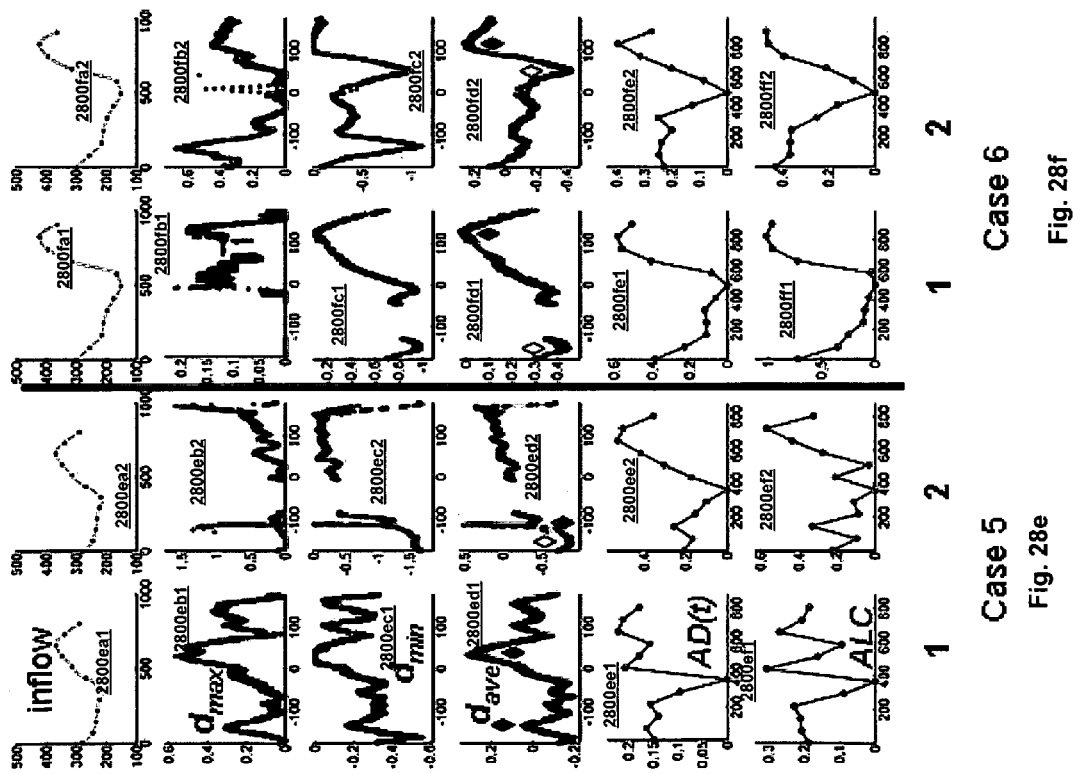
FIG. 28e is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
FIG. 28f is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.
Figure 28G:
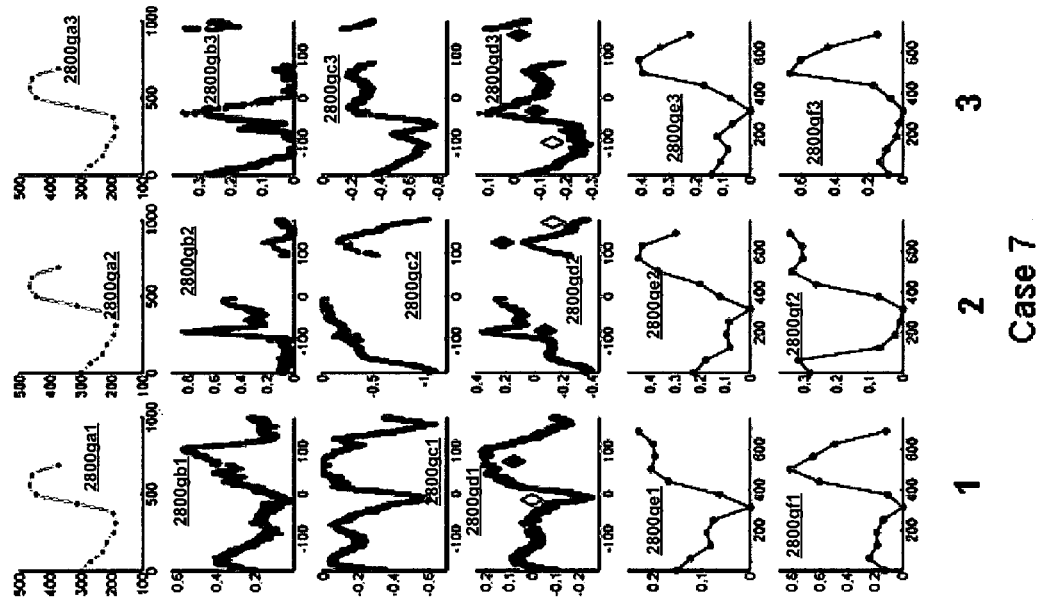
FIG. 28g is an illustration of the volumetric flow rate in the proximal section of the parent artery of a cerebral aneurysm, the maximum distension, the maximum contraction, the average lumen displacement, the time averaged lumen displacement, and the displacement of the lumen for an aneurysm of a subject during a cardiac cycle.

Referring to FIG. 22, in an exemplary experimental implementation of the method 1500, after completing 1516, the volumetric flow rate 1516a within the lumen 1510aa of the proximal parent artery of the aneurysm was generated for a complete cardiac cycle, or other selected time period.

Referring to FIG. 23, in an exemplary experimental implementation of the method 1500, the color-coded volumetric flow rate 2300 within the lumen 1510aa of the proximal parent artery of the aneurysm was generated. In the exemplary experimental embodiment, as illustrated in FIG. 23, the green data points included an acceleration phase from minimum to maximum inflow, and the red data points included a deceleration phase from maximum inflow to minimum inflow.

Referring to FIG. 24, in an exemplary experimental implementation of the method 1500, corresponding schematic aneurysm boundaries 2400a, 2400b, and 2400c were generated, for representative data points color-coded according to the color scheme for the volumetric inflow waveform illustrated in FIG. 23. In an exemplary experimental embodiment, the boundary 2400a, in dark red, illustrated a wall boundary at average inflow superimposed on a wall boundary for minimum inflow, the boundary 2400b, in green, illustrated a wall boundary at minimum inflow ($r_0$), and the boundary 2400c, in bright red, illustrated a wall boundary at maximum inflow superimposed on a wall boundary for minimum inflow. The origin of the wall boundaries, 2400a, 2400b, and 2400c, is denoted by O, and the corresponding wall distension and wall contractions di(t), i: boundary point index, I=1, . . . , n, are indicated by filled and dashed lines respectively. The maximum contraction $d_{min}$ is shown in bright blue, in the boundary 2400a, and the maximum distension $d_{max}$ is shown in pink, in the boundary 2400c. The angles for maximum distension and maximum contractions, $a_{max}$ and $a_{min}$, respectively, are shown in dark blue in the boundaries, 2400a and 2400c.

Referring to FIG. 25, in an exemplary experimental implementation of the method 1500, the total average displacement, 2500a, 2500b, and 2500c, for three of the time points, $t_1$, $t_6$, and $t_{10}$, respectively, was generated.

Referring to FIG. 26, in an exemplary experimental implementation of the method 1500, a time-averaged wall boundary 2600a, in gray, $d_{ave}$, was superimposed on the wall boundary for minimum inflow 2600b, in green, with origin denoted by O. The time averaged displacement $d_{avei}$ for each boundary point i was calculated as the average over all time points, and $d_{max}$ and $d_{min}$ are found as maximum and minimum, negative, respectively, of all $d_i(t_k)$, i=1, . . . , n; k=1, . . . , 12.

Referring to FIGS. 27a, 27b, 27c, 27d, 27e, 27f, and 27g, in an exemplary experimental implementation of the method 1500 was performed on subjects 1, 2, 3, 4, 5, 6, and 7, respectively, each having corresponding vasculature 2700a, 2700b, 2700c, 2700d, 2700e, 2700f and 2700g, respectively, and each having corresponding aneurysms, 2700*aa*, 2700*ba*, 2700*ca*, 2700*da*, 2700*ea*, 2700*fa*, and 2700*ga*, respectively.

As illustrated in FIGS. 27*a*, 27*b*, 27*c*, 27*d*, 27*e*, 27*f*, and 27*g*, in an exemplary experimental implementation of the method 1500, for each of the subjects 1, 2, 3, 4, 5, 6, and 7, respectively, the color-coded aneurismal boundaries, 2700*ab*1 and 2700*ab*2, 2700*bb*1 and 2700*bb*2, 2700*cb*1 and 2700*cb*2, 2700*db*1 and 2700*db*2, 2700*eb*1 and 2700*eb*2, 2700*fb*1 and 2700*fb*2, and 2700*gb*1, 2700*gb*2 and 2700*gb*3, respectively, were calculated and were overlayed on the corresponding time averaged MRI cross sectional images, 2700*ac*1 and 2700*ac*2, 2700*bc*1 and 2700*bc*2, 2700*cc*1 and 2700*cc*2, 2700*dc*1 and 2700*dc*2, 2700*ec*1 and 2700*ec*2, 2700*fc*1 and 2700*fc*2, and 2700*gc*1, 2700*gc*2 and 2700*gc*3, respectively, of the corresponding aneurysms, 2700*aa*, 2700*ba*, 2700*ca*, 2700*da*, 2700*ea*, 2700*fa*, and 2700*ga*, respectively.

As illustrated in FIGS. 27*a*, 27*b*, 27*c*, 27*d*, 27*e*, 27*f*, and 27*g*, in an exemplary experimental implementation of the method 1500, for each of the subjects 1, 2, 3, 4, 5, 6, and 7, respectively, the green boundaries denoted an accelerating phase from minimum flow to maximum flow, and the green boundaries denoted a decelerating flow from maximum to minimum flow. As illustrated in FIGS. 27*a*, 27*b*, 27*c*, 27*d*, 27*e*, 27*f*, and 27*g*, in an exemplary experimental implementation of the method 1500, for each of the subjects 1, 2, 3, 4, 5, 6, and 7, respectively, the white arrows marked the location of absolute maximum distension and the black arrows marked the location of absolute maximum contraction for each cross section of the corresponding aneurysms.

As illustrated in FIGS. 28*a*, 28*b*, 28*c*, 28*d*, 28*e*, 28*f*, and 28*g*, in an exemplary experimental implementation of the method 1500, for each of the subjects 1, 2, 3, 4, 5, 6, and 7, respectively, the following results were obtained:

The teachings of the present exemplary embodiments may also be employed as a diagnostic tool for detecting, monitoring, and predicting disease processes in patients such as, for example, aortic and thoracic aneurysms. Aortic aneurysms are abnormal enlargements of the abdominal aorta. Thoracic aneurysms occur at the ascending aorta and abdominal aortic aneurysms ("AAA") are located at the descending aorta. Similar to the approach discussed above with reference to the exemplary embodiment, the methods 100 and 1500 can be used to quantify the wall motion of aortic aneurysms and to correlate this motion with the aortic flow waveform. Motion of the AAA wall is of particular interest for the design of endografts which are metal coils and tubes that are being placed inside the AAA for restoring the abdominal aorta. A better understanding of the aortic wall motion will be helpful in designing improved endografts with better mechanical properties for a better treatment outcome.

The teachings of the present exemplary embodiments may also be employed as a diagnostic tool for detecting, monitoring, and predicting disease processes in patients such as, for example, peripheral arterial disease ("PAD"), a marker for systemic vascular disease and a major cause of morbidity and mortality, which is present in 20% of the U.S. population. Atherosclerosis of the superficial femoral arteries ("SFA") is considered a major cause of PAD of the legs. The teachings of the present exemplary embodiment can be utilized to characterize wall motion of the SFA and therefore also motion of the atherosclerotic plaque contained within the wall of the SFA. Potential applications of the teachings of the exemplary embodiments also include determining risk factors for plaque rupture based on plaque motion and the creation of emboli originating from the plaque surface responsible for vessel occlusion downstream.

The teachings of the present exemplary embodiments may also be employed as a diagnostic tool for detecting, monitoring, and predicting disease processes in patients such as, for

| Subject | Aneurysm Cross Section | Inflow Volumetric Waveform | $d_{max}$ Maximum Distention | $d_{min}$ Maximum Contraction | $d_{ave}$ Average Displacement | AD(t) Temporal Average Displacement | ALC Displacement Of Aneurysm Lumen Boundary |
|---|---|---|---|---|---|---|---|
| 1 | 2700ac1 | 2800aa1 | 2800ab1 | 2800ac1 | 2800ad1 | 2800ae1 | 2800af1 |
| 1 | 2700ac2 | 2800aa2 | 2800ab2 | 2800ac2 | 2800ad2 | 2800ae2 | 2800af2 |
| 2 | 2700bc1 | 2800ba1 | 2800bb1 | 2800bc1 | 2800bd1 | 2800be1 | 2800bf1 |
| 2 | 2700bc2 | 2800ba2 | 2800bb2 | 2800bc2 | 2800bd2 | 2800be2 | 2800bf2 |
| 3 | 2700cc1 | 2800ca1 | 2800cb1 | 2800cc1 | 2800cd1 | 2800ce1 | 2800cf1 |
| 3 | 2700cc2 | 2800ca2 | 2800cb2 | 2800cc2 | 2800cd2 | 2800ce2 | 2800cf2 |
| 4 | 2700dc1 | 2800da1 | 2800db1 | 2800dc1 | 2800dd1 | 2800de1 | 2800df1 |
| 4 | 2700dc2 | 2800da2 | 2800db2 | 2800dc2 | 2800dd2 | 2800de2 | 2800df2 |
| 5 | 2700ec1 | 2800ea1 | 2800eb1 | 2800ec1 | 2800ed1 | 2800ee1 | 2800ef1 |
| 5 | 2700ec2 | 2800ea2 | 2800eb2 | 2800ec2 | 2800ed2 | 2800ee2 | 2800ef2 |
| 6 | 2700fc1 | 2800fa1 | 2800fb1 | 2800fc1 | 2800fd1 | 2800fe1 | 2800ff1 |
| 6 | 2700fc2 | 2800fa2 | 2800fb2 | 2800fc2 | 2800fd2 | 2800fe2 | 2800ff2 |
| 7 | 2700gc1 | 2800ga1 | 2800gb1 | 2800gc1 | 2800gd1 | 2800ge1 | 2800gf1 |
| 7 | 2700gc2 | 2800ga2 | 2800gb2 | 2800gc2 | 2800gd2 | 2800ge2 | 2800gf2 |
| 7 | 2700gc3 | 2800ga3 | 2800gb3 | 2800gc3 | 2800gd3 | 2800ge3 | 2800gf3 |

As illustrated in FIGS. 28*a*, 28*b*, 28*c*, 28*d*, 28*e*, 28*f*, and 28*g*, in an exemplary experimental implementation of the method 1500, for each of the subjects 1, 2, 3, 4, 5, 6, and 7, respectively, the color coding in the graphical illustrations of $d_{max}$, $d_{min}$ and $d_{ave}$ correspond to the color coding in the graphical illustrations of the volumetric inflow waveform and thereby allows identification of the time of maximum distension and maximum contraction for section of the corresponding aneurysmal wall.

The teachings of the present exemplary embodiments may also be employed as a diagnostic tool for detecting, monitorexample, wall motion of atherosclerotic plaque in the carotid bifurcation. Atherosclerosis at this anatomical location is a major risk factor for stroke. Plaque mobility may be indicative of plaque rupture and the creation of emboli traveling into the cerebral vasculature causing transient ischemic stroke events ("TIA").

The teaching of the present exemplary embodiments may also be application to the diagnosis of acute aortic dissections. In particular, the parameters provided by the exemplary embodiments can be utilized to diagnose an acute aortic dissection in contrast to a chronic aortic dissection. This is of importance as treatment outcome of an aortic dissection is much better is treatment occurs during the early phase of the disease, i.e. while the dissection is acute. For an acute dissection, larger motion of the aortic boundary, and especially the wall separating the true and false lumen (the septum), will be higher as the septum is more flexible. Consequently, treatment, consisting of placing a stent to enlarge the true lumen will have a higher chance to succeed than in a chronic dissection, where the septum is thick and not mobile any more. In the latter case, the force exerted by the stent will be insufficient to appose the septum to the aortic wall.

The teaching of the present exemplary embodiments may also be application to the diagnosis of cerebral aneurysms. In particular, large variations in contractions and distensions over the cardiac cycle on a certain location of the aneurysmal wall may be indicative of a thin wall segment that is prone to rupture. Aneurysm rupture will result in subarachnoid hemorrhage which has a 50% rate of mortality. Currently, there is no reliable method to accurately assess rupture risk of an individual cerebral aneurysm. The exemplary embodiments may permit a medical professional to identify those aneurysms with a high risk of rupture, which are the ones with high aneurysmal wall motion. This may result in lowering treatment costs, as currently each aneurysm is being treated. It may also lower risk to the patient, as the treatment of cerebral aneurysms currently bears a risk of about 10%.

It is understood that variations may be made in the above without departing from the scope of the invention. For example, the teachings of the present exemplary embodiments may be applied to characterize the dynamics of vascular disease in general regardless of the location within the body. While specific embodiments have been shown and described, modifications can be made by one skilled in the art without departing from the spirit or teaching of this invention. The embodiments as described are exemplary only and are not limiting. Many variations and modifications are possible and are within the scope of the invention. Accordingly, the scope of protection is not limited to the embodiments described, but is only limited by the claims that follow, the scope of which shall include all equivalents of the subject matter of the claims.

The invention claimed is:

1. A computer implemented method of processing MRI images to determine one or more characteristics of an anatomical feature, comprising:
   obtaining one or more first MRI images of the anatomical feature;
   identifying a boundary of the anatomical feature in the first MRI images;
   using the identified boundary to mask one or more corresponding second MRI images of the anatomical feature to isolate the anatomical feature within the second MRI images;
   determining by a computer an average displacement for a center of the anatomical feature;
   determining by the computer an average displacement for each boundary point of the identified boundary over time; and
   using by the computer the average displacement for each boundary point to determine a total average displacement of the identified boundary.

2. The method of claim 1, wherein the anatomical feature comprises one or more of the following: a lumen of an aorta or a lumen of an aneurysm.

3. The method of claim 1, wherein the first MRI images comprise MRI magnitude images.

4. The method of claim 1, wherein the second MRI images comprise MRI phase images.

5. The method of claim 1, wherein the anatomical feature comprises a lumen; and wherein identifying a boundary of the lumen in the second MRI images comprises determining a contiguous area within the second MRI images having increased fluid flow relative to other areas in the second MRI images.

6. The method of claim 1, further comprising:
   identifying the center of the anatomical feature.

7. The method of claim 1, further comprising:
   determining a volumetric flow rate within the identified boundary of the anatomical feature.

8. The method of claim 7, wherein determining a volumetric flow rate within the identified boundary of the anatomical feature comprises multiplying an average pixel intensity level within the identified boundary by the cross sectional area of the identified boundary.

9. The method of claim 1,
   wherein the average displacement for the center or the average displacement for each boundary point is determined during a cardiac cycle.

10. The method of claim 1, further comprising:
    determining a volumetric flow rate through the anatomical feature over time; and
    correlating the average displacement for the center or the average displacement for each boundary point with the volumetric flow rate.

11. The method of claim 1, further comprising:
    determining a maximum distention of the identified boundary of the anatomical feature over time.

12. The method of claim 11, further comprising:
    determining a maximum contraction of the identified boundary of the anatomical feature over time.

13. The method of claim 1, further comprising:
    determining a maximum contraction of the identified boundary of the anatomical feature over time.

14. A computer readable medium storing a computer program for processing MRI images to determine one or more characteristics of an anatomical feature, the computer program when executed causing a computer to:
    obtain one or more first MRI images of the anatomical feature;
    identify a boundary of the anatomical feature in the first MRI images;
    use the identified boundary to mask one or more corresponding second MRI images of the anatomical feature to isolate the anatomical feature within the second MRI images;
    determine an average displacement for a center of the anatomical feature over time;
    determine an average displacement for each boundary point of the identified boundary over time; and
    use the average displacement for each boundary point to determine a total average displacement of the identified boundary.

15. The computer readable medium of claim 14, wherein the anatomical feature comprises one or more of the following: a lumen of an aorta or a lumen of an aneurysm.

16. The computer readable medium of claim 14, wherein the first MRI images comprise MRI magnitude images.

17. The computer readable medium of claim 14, wherein the second MRI images comprise MRI phase images.

18. The computer readable medium of claim 14, wherein the anatomical feature comprises a lumen; and wherein identifying a boundary of the lumen in the second MRI images comprises determining a contiguous area within the second MRI images having increased fluid flow relative to other areas in the second MRI images.

19. The computer readable medium of claim 14, the computer program when executed further causing the computer to:
identify the center of the anatomical feature.

20. The computer readable medium of claim 14, the computer program when executed further causing the computer to:
determine a volumetric flow rate within the identified boundary of the anatomical feature.

21. The computer readable medium of claim 20, wherein determining a volumetric flow rate within the identified boundary of the anatomical feature comprises multiplying an average pixel intensity level within the identified boundary by the cross sectional area of the identified boundary.

22. The computer readable medium of claim 14,
wherein the average displacement for the center or the average displacement for each boundary point is determined during a cardiac cycle.

23. The computer readable medium of claim 14, the computer program when executed further causing the computer to:
determine a volumetric flow rate through the anatomical feature over time; and
correlate the average displacement for the center or the average displacement for each boundary point with the volumetric flow rate.

24. The computer readable medium of claim 14, the computer program when executed further causing the computer to:
determine a maximum distention of the identified boundary of the anatomical feature over time.

25. The computer readable medium of claim 24, the computer program when executed further causing the computer to:
determine a maximum contraction of the identified boundary of the anatomical feature over time.

26. The computer readable medium of claim 14, the computer program when executed further causing the computer to:
determine a maximum contraction of the identified boundary of the anatomical feature over time.

27. A computer implemented method for processing MRI images, comprising:
displaying an MRI image including an anatomical feature;
calculating a boundary of the anatomical feature using the MRI image;
displaying the calculated boundary of the anatomical feature overlayed onto the MRI image;
determining by a computer an average displacement for a center of the anatomical feature over time;
determining by the computer an average displacement for each boundary point of the calculated boundary of the anatomical feature over time; and
using by the computer the average displacement for each boundary point to determine a total average displacement of the calculated boundary.

28. The method of claim 27, wherein the MRI image comprises a time averaged MRI image.

29. The method of claim 28, wherein the calculated boundary of the anatomical feature overlayed on the MRI image comprises a time sequence of calculated boundaries.

30. The method of claim 27, wherein the boundary of the calculated anatomical feature overlayed on the MRI image comprises a time sequence of calculated boundaries.

31. A computer readable medium storing a computer program for processing MRI images, the computer program when executed causing a computer to:
display an MRI image including an anatomical feature;
calculate a boundary of the anatomical feature using the MRI image;
display the calculated boundary of the anatomical feature overlayed onto the MRI image;
determine an average displacement for a center of the anatomical feature over time;
determine an average displacement for each boundary point of the calculated boundary of the anatomical feature over time; and
use the average displacement for each boundary point to determine a total average displacement of the calculated boundary.

32. The computer readable medium of claim 31, wherein the MRI image comprises a time averaged MRI image.

33. The computer readable medium of claim 32, wherein the calculated boundary of the anatomical feature overlayed on the MRI image comprises a time sequence of calculated boundaries.

34. The computer readable medium of claim 31, wherein the calculated boundary of the anatomical feature overlayed on the MRI image comprises a time sequence of calculated boundaries.

35. A computer implemented method for processing MRI images to diagnose an acute aortic dissection in a patient, comprising:
obtaining an MRI image of the aorta of the patient;
determining by a computer an average displacement for a center of the aorta;
calculating a boundary of the lumen of the aorta MRI image; and
determining by the computer an average displacement for each boundary point of the lumen boundary;
using by the computer the average displacement for each boundary point to determine a degree of total average displacement of the lumen boundary of the MRI image of the aorta during a cardiac cycle; and
if the degree of total average displacement is greater than a threshold value, then diagnosing that the patient has an acute aortic dissection.

36. The method of claim 35, wherein the average displacement for each boundary point comprises contractions and distentions of the lumen boundary.

37. A computer readable medium storing a computer program for processing MRI images to diagnose an acute aortic dissection in a patient, the computer program when executed causing a computer to:
obtain an MRI image of the aorta of the patient;
determine an average displacement for a center of the aorta;
calculate a boundary of the lumen of the aorta MRI image during the cardiac cycle; and
determine an average displacement for each boundary point of the lumen boundary;
use the average displacement for each boundary point to determine a degree of total average displacement of the lumen boundary of the MRI image of the aorta during the cardiac cycle; and
if the degree of total average displacement is greater than a threshold value, then diagnose that the patient has an acute aortic dissection.

38. The computer readable medium of claim 37, wherein the average displacement for each boundary point comprises contractions and distentions of the lumen boundary.

39. A computer implemented method for processing MRI images to diagnose a cerebral aneurysm in a patient, comprising:
- obtaining an MRI image of the cerebral aneurysm of the patient;
- determining by a computer an average displacement for a center of the cerebral aneurysm over time;
- calculating a boundary of the lumen of the cerebral aneurysm MRI image; and
- determining by the computer an average displacement for each boundary point of the lumen boundary;
- using by the computer the average displacement for each boundary point to determine a degree of total average displacement of the lumen boundary of the MRI image of the cerebral aneurysm during a cardiac cycle; and
- if the degree of total average displacement is greater than a threshold value, then diagnosing that the patient has the cerebral aneurysm.

40. The method of claim 39, wherein the average displacement for each boundary point comprises contractions and distentions of the lumen boundary.

41. A computer readable medium storing a computer program for processing MRI images to diagnose a cerebral aneurysm in a patient, the computer program when executed causing a computer to:
- obtain an MRI image of the cerebral aneurysm of the patient;
- determine an average displacement for a center of the cerebral aneurysm over time;
- calculate a boundary of the lumen of the cerebral aneurysm MRI image during the cardiac cycle; and
- determine by the computer an average displacement for each boundary point of the lumen boundary;
- use the average displacement for each boundary point to determine a degree of total average displacement of the lumen boundary of the MRI image of the cerebral aneurysm during the cardiac cycle; and
- if the degree of total average displacement is greater than a threshold value, then diagnose that the patient has the cerebral aneurysm.

42. The computer readable medium of claim 41, wherein the average displacement for each boundary point comprises contractions and distentions of the lumen boundary.

43. A computer implemented method of processing MRI images to determine one or more characteristics of an anatomical feature, comprising:
- obtaining one or more first MRI images of the anatomical feature;
- filtering by a computer the first MRI images using a spatial bandpass filter to generate filtered MRI images;
- filtering by the computer the filtered MRI images using a median filter to generate MRI magnitude images;
- identifying a boundary of the anatomical feature in the MRI magnitude images;
- using the identified boundary to mask one or more corresponding second MRI images of the anatomical feature to isolate the anatomical feature within the second MRI images;
- determining a volumetric flow rate through the anatomical feature over time;
- determining by the computer a displacement for a center of the anatomical feature at each cross section over time;
- determining by the computer an average displacement for the anatomical feature based on the displacement for the center at each cross section;
- correlating the average displacement for the anatomical feature with the volumetric flow rate;
- determining by the computer a maximum distention and a maximum contraction for each boundary point of the identified boundary over time;
- determining by the computer an average displacement for each boundary point of the identified boundary over time;
- correlating the average displacement for each boundary point with the volumetric flow rate by determining a localized motion of the identified boundary based on the maximum distention and the maximum contraction for each boundary point; and
- using by the computer the average displacement for each boundary point to determine a total average displacement of the identified boundary.

44. The method of claim 43, wherein the anatomical feature comprises one or more of the following: a lumen of an aorta or a lumen of an aneurysm.

45. The method of claim 43, wherein the second MRI images comprise MRI phase images.

46. The method of claim 43, wherein the anatomical feature comprises a lumen; and wherein identifying a boundary of the lumen in the second MRI images comprises determining a contiguous area within the second MRI images having increased fluid flow relative to other areas in the second MRI images.

47. The method of claim 43, further comprising:
identifying the center of the anatomical feature.

48. The method of claim 43, wherein determining a volumetric flow rate through the anatomical feature comprises multiplying an average pixel intensity level within the identified boundary by the cross sectional area of the identified boundary.

49. The method of claim 43, wherein the average displacement for the center or the average displacement for each boundary point is determined during a cardiac cycle.

50. A computer readable medium storing a computer program for processing MRI images, the computer program when executed causing a computer to:
- obtain one or more first MRI images of the anatomical feature;
- filter by a computer the first MRI images using a spatial bandpass filter to generate filtered MRI images;
- filter by the computer the filtered MRI images using a median filter to generate MRI magnitude images;
- identify a boundary of the anatomical feature in the MRI magnitude images;
- use the identified boundary to mask one or more corresponding second MRI images of the anatomical feature to isolate the anatomical feature within the second MRI images;
- determine a volumetric flow rate through the anatomical feature over time;
- determine by the computer a displacement for a center of the anatomical feature at each cross section over time;
- determine by the computer an average displacement for the anatomical feature based on the displacement for the center at each cross section;
- correlate the average displacement for the anatomical feature with the volumetric flow rate;
- determine by the computer a maximum distention and a maximum contraction for each boundary point of the identified boundary over time;
- determine by the computer an average displacement for each boundary point of the identified boundary over time;
- correlate the average displacement for each boundary point with the volumetric flow rate by determining a localized motion of the identified boundary based on the maximum distention and the maximum contraction for each boundary point; and use the average displacement for each boundary point to determine by the computer a total average displacement of the identified boundary.

51. The computer readable medium of claim 50, wherein the anatomical feature comprises one or more of the following: a lumen of an aorta or a lumen of an aneurysm.

52. The computer readable medium of claim 50, wherein the second MRI images comprise MRI phase images.

53. The computer readable medium of claim 50, wherein the anatomical feature comprises a lumen; and wherein identifying a boundary of the lumen in the second MRI images comprises determining a contiguous area within the second MRI images having increased fluid flow relative to other areas in the second MRI images.

54. The computer readable medium of claim 50, the computer program when executed further causing the computer to:

identify the center of the anatomical feature.

55. The computer readable medium of claim 50, wherein determining a volumetric flow rate through the anatomical feature comprises multiplying an average pixel intensity level within the identified boundary by the cross sectional area of the identified boundary.

56. The computer readable medium of claim 50, wherein the average displacement for the center or the average displacement for each boundary point is determined during a cardiac cycle.

* * * * *